US007048893B2

(12) United States Patent
Bellon

(10) Patent No.: US 7,048,893 B2
(45) Date of Patent: May 23, 2006

(54) MASK FOR DEPOSITING AND DISTRIBUTING REAGENTS ON AN ANALYTICAL SUPPORT

(75) Inventor: Franck Bellon, Longjumeau (FR)

(73) Assignee: Sebia (FR)

( * ) Notice: Subject to any disclaimer, the term of this patent is extended or adjusted under 35 U.S.C. 154(b) by 210 days.

(21) Appl. No.: 10/359,323

(22) Filed: Feb. 6, 2003

(65) Prior Publication Data

US 2003/0175989 A1 Sep. 18, 2003

Related U.S. Application Data

(63) Continuation-in-part of application No. 10/072,327, filed on Feb. 6, 2002, now abandoned.

(51) Int. Cl.

| | |
|---|---|
| ***B01L 3/02*** | (2006.01) |
| ***B01L 3/00*** | (2006.01) |
| ***G01N 1/10*** | (2006.01) |
| ***G01N 35/00*** | (2006.01) |
| ***C12M 1/34*** | (2006.01) |

(52) U.S. Cl. .......................... 422/100; 422/61; 422/63; 422/65; 422/66; 436/180; 436/46; 435/288.3; 435/287.3; 435/307.1; 204/604

(58) Field of Classification Search .......... 422/99–100, 422/61, 63, 65, 66; 436/180, 46; 435/288.3, 435/287.3, 307.1; 204/604; 347/40, 44

See application file for complete search history.

(56) References Cited

U.S. PATENT DOCUMENTS

| | | | | |
|---|---|---|---|---|
| 5,000,921 A * | 3/1991 | Hanaway et al. | ........... | 422/100 |
| 5,009,846 A * | 4/1991 | Gavet et al. | .................. | 422/56 |
| 5,137,614 A | 8/1992 | Golias | | |
| 5,238,651 A | 8/1993 | Chuba | | |
| 5,403,456 A | 4/1995 | Bellon | | |
| 5,464,521 A | 11/1995 | Bellon | | |
| 6,255,119 B1 * | 7/2001 | Baier | ......................... | 436/180 |

(Continued)

FOREIGN PATENT DOCUMENTS

EP 0 526 271 B1 6/1992

(Continued)

OTHER PUBLICATIONS

Alper & Johnson, Immunofixation Electrophoresis: A technique for the study of protein polymorphism, 17 AM Vox. Sang, 445-52 (1969).

(Continued)

*Primary Examiner*—Jill Warden
*Assistant Examiner*—Brian R Gordon
(74) *Attorney, Agent, or Firm*—Lerner, David, Littenberg, Krumholz & Mentlik, LLP

(57) ABSTRACT

The invention concerns a mask for distributing reagents on an analytical support, such as an electrophoresis gel, the mask having a body with parallel upper and lower surfaces, a plurality of lanes located on the lower surface of the mask have wedge-shaped projecting elements with a sloped surface between first and second ends thereof, an opening extends from the upper surface of the body of the mask to the lowest point of the sloped surface. The mask is positioned over an analytical support and loaded with the desired reagents which are held by capillary action between the mask and the analytical support. The mask can then be moved in a sweeping motion across the analytical support to deposit the reagents thereon. In another embodiment, the projecting elements are rectangular in shape and the mask is positioned at an incline with respect the analytical support.

32 Claims, 15 Drawing Sheets

U.S. PATENT DOCUMENTS

| | | | | |
|---|---|---|---|---|
| 6,326,212 | B1 * | 12/2001 | Aoki | 436/180 |
| 6,368,562 | B1 * | 4/2002 | Yao | 422/101 |
| 6,416,719 | B1 * | 7/2002 | Fawcett et al. | 422/104 |
| 6,491,873 | B1 * | 12/2002 | Roberts et al. | 422/101 |
| 6,632,660 | B1 * | 10/2003 | Ramstad | 435/305.2 |
| 6,838,051 | B1 * | 1/2005 | Marquiss et al. | 422/63 |
| 2002/0159918 | A1 * | 10/2002 | Tseng et al. | 422/100 |
| 2002/0182114 | A1 * | 12/2002 | Ingenhoven et al. | 422/99 |
| 2003/0143124 | A1 * | 7/2003 | Roberts et al. | 422/102 |
| 2004/0071602 | A1 * | 4/2004 | Yiu | 422/100 |

FOREIGN PATENT DOCUMENTS

| | | |
|---|---|---|
| EP | 0 666 476 | 8/1995 |
| EP | 0 526 627 B1 | 4/1996 |
| EP | 1 048 949 | 11/2000 |
| GB | 2 261 508 | 5/1993 |
| WO | WO 92/14495 | 9/1992 |
| WO | WO-97/30347 | 8/1997 |

OTHER PUBLICATIONS

Cawlay et al., Immunofixation electroporetic techniques applied to identification of proteins in serum and cerebrospinal fluid, 22 Clin. Chem. 1262-68 (1976).

Ritchie & Smith, Immunofixation. I. General Principles and Application to Agarose Gel Electrophoresis, 22 Clin. Chem. 479-99 (1976).

* cited by examiner

MASK FOR DEPOSITING AND DISTRIBUTING REAGENTS ON AN ANALYTICAL SUPPORT

CROSS-REFERENCE TO RELATED APPLICATIONS

The present application is a continuation-in-part of U.S. patent application Ser. No. 10/072,327, filed on Feb. 6, 2002, now abandoned the contents of which is hereby incorporated by reference herein.

BACKGROUND OF THE INVENTION

The invention relates to a mask for depositing and distributing one or more reagents on an analytical support, in particular a support for electrophoresis, for example agarose gel.

The invention is suitable for use, for example, in the field of detecting and characterizing constituents present in a biological sample, in particular a biological liquid such as serum, urine or cerebrospinal fluid. In particular, such detection can be carried out following separation of said constituents from a biological sample, for example, using electrophoresis. Detection can then be carried out in particular using known immunofixation techniques, which require bringing reagents into contact with the constituents separated from the sample and incubating them to produce an immunological recognition reaction of the constituents separated from the biological sample with the reagents in predetermined zones of an analytical support.

The invention is advantageously used for routine analyses, particularly of the type carried out in the context of clinical analyses.

The invention also relates to a mask intended for depositing and distributing one or more reagents on an analytical support, associated in a device with positioning means that allow the mask to be positioned with respect to the analytical support, in the proximity of said support, when the mask is used to deposit and distribute the reagents.

These positioning means can also be associated with guide means or can comprise guide means for displacing the mask when it is positioned in the proximity of the analytical support, to allow the reagents to be distributed onto delimited zones of the support, including zones designated for incubation of the reagents with the constituents of the sample.

The device of the invention allows reagents to be deposited or distributed manually. It can also be arranged for automated deposition of these reagents and optionally for automated distribution.

In some embodiments of the invention, the step for loading the reagents into the mask can also be carried out manually or in an automated manner. Advantageously, the mask of the invention is more easily loaded than available prior art masks.

In a further aspect, the invention provides a method for depositing and distributing reagents on an analytical support.

In one particular implementation of the invention, the method is used to deposit and distribute reagents intended to carry out immunofixation to detect and possibly quantify specific constituents contained in a biological sample, said constituents having already been separated by electrophoresis on a support such as agarose gel.

The invention also concerns an immunofixation method employing said mask.

In a further aspect, the invention provides a kit comprising a mask in accordance with the invention.

A kit in accordance with the invention is advantageously adapted to carry out an immunofixation method using the mask of the invention.

The invention also concerns means for positioning and guiding the mask.

It should be remembered that immunofixation, which can analyse biological samples with a view to typing the paraproteins they contain, is a widely practised routine analysis carried out in clinical analysis laboratories in particular.

That technique, which combines electrophoresis with the formation of precipitates on the electrophoresis gel, has been known for a long time. The technique has in particular been described by Alper C A and Johnson A M Vox. Sang. 17: 445 (1969), Cawley L P et al., Clin. Chem. 22: 1262 (1976), Ritchie R F and Smith R Clin. Chem. 22: 497, 1735, 1982 (1976). It allows the identification of anomalies in different biological samples, in particular in biological liquids, for example serum, urine or cerebrospinal fluid.

The technique principally comprises the following steps:

1) separating protein constituents from the test serum or liquid by electrophoresis on a support such as a gel, for example agarose gel;

2) an immunological reaction with specific antibodies for the separated proteins;

3) revealing the immunological complexes formed.

The conditions for carrying out these steps have been described in the prior art.

The devices used also comprise the possibility of producing a reference lane (track) on the same electrophoresis support, in particular on the same gel, obtained by fixing all of the separated proteins present on the sample using a protein fixative including, for example, a polyvalent antiserum.

New semi-automatic techniques for applying the biological samples to be analyzed, for migration under controlled temperature and for depositing the reagents (including, for example, the antiserums and fixatives) allow immunofixation profiles to be miniaturized while keeping the sensitivities and resolutions satisfactory. Miniaturization allows a larger number of samples to be analyzed on the same electrophoresis support, in particular on the same gel.

Thus, in a few years we have advanced from carrying out one to carrying out nine immunofixations on a single 8×10 cm electrophoresis gel (using, for example, an immunofixation kit sold by SEBIA under the trademark Hydragel 9 IF). This saves time as regards the analysis and reduces reagent consumption, resulting in a reduction in analytical costs.

To deposit the reagents with a view to carrying out immunofixation under such conditions, European patent EP-B1-0 526 271, for example, describes a mask or device for distributing reagents, generally specific antiserums and a fixative, that can overcome some of the problems posed by prior art devices or masks and that is safer and easier to use. Thus, to carry out 9 immunofixations, for example, on the same electrophoresis gel in three rows of three samples using the mask described in EP-B1-0 0 526 271, for each sample, 6 reagents have to be pipetted out (fixative, anti-IgG antiserum, anti-IgA antiserum, anti-IgM antiserum, anti-k antiserum and anti-λ antiserum), i.e., a total of 54 pipetting operations.

These manual pipetting operations can prove to be long and difficult even if repetitive dosing pipettes are used.

The primary aim of the present invention is to improve the conditions for depositing and distributing reagents on an analytical support using masks, by proposing a mask that can reduce the number of reagent pipetting operations and which can reduce the quantity of reagents used. The means proposed in the context of the invention can be used in any analytical technique requiring controlled deposition of reagents on an analytical support. In this respect, the following techniques can be mentioned: immunofixation following electrophoretic separation; or distribution onto a specific substrate for enzymatic developing, for example for assaying lactodehydrogenase (LDH) or creatine kinase (CK).

SUMMARY OF THE INVENTION

In a first aspect, the invention provides a mask for depositing and distributing reagents on an analytical support the design of which takes into account its use including its displacement to carry out the step of distributing reagents onto predetermined zones on an analytical support. The mask of the invention can therefore be considered to be a movable mask when in use.

The present invention also limits reagent consumption, in particular that of antiserums, which are expensive products, and fixative in the case of immunofixation reactions, and can thus reduce the cost of the analyses carried out. It also facilitates loading the reagents into the mask, in particular by limiting the number of pipetting operations and/or by enabling the mask to be loaded automatically.

Further, the proposed mask ensures a consistent quality of the result, under improved or even simplified manipulation conditions. In particular, after the phase for incubating the reagents distributed using the device of the invention, it is no longer necessary to eliminate excess reagents that remain between the gel and the mask, as is the case when using a mask proposed in EP-B1-0 526 271

With the mask of the invention, after spreading and distributing the reagents, no more free reagent is present between the mask and analytical support, as all of the reagents that were initially introduced have been deposited on the analytical support. Thus, it is not necessary to pump off any excess reagents that may be present on the analytical support.

Thus, the invention provides a mask for depositing and distributing reagents on an analytical support for analyzing biological samples, comprising:

a lower surface and an upper surface that are at least partially mutually parallel, separated by a distance constituting the thickness of the mask;

one or more delimited zones (lanes) located on the level of the lower surface of the mask and comprising an element that projects (projecting element) from the lower surface of the mask, each projecting element comprising a portion constituting a slope with respect to a horizontal plane;

associated with each lane, an opening traversing the mask over the whole of its thickness from an upper orifice on the upper surface of the mask to a lower orifice, said lower orifice being located in the lane in the proximity of the lowest point of the slope of the lane;

the mask being such that the lane or lanes it comprises can hold reagents loaded into each opening and deposited on the analytical support by capillary action between the lane and the surface of the analytical support facing which the mask is to be placed.

The expression "mask" as used in the present invention generally designates a plate designed to allow positioning in alignment with delimited zones on an analytical support, if necessary in conjunction with associated means, in which reagents must be deposited and distributed when they are loaded into the mask and brought into contact with the delimited zones.

BRIEF DESCRIPTION OF THE DRAWINGS

Other characteristics, advantages and details of the invention will become apparent from the following description, made with reference to the accompanying drawings, in which:

FIG. 9: top view of the guide permitting to position the mask above the electrophoresis support and to displace the mask above the support (gel) in a given direction and on a given stoke;

FIG. 10: Top and bottom views of the carriage which is mounted on the rail 14 by means of a slide 49. The carriage has four feet 30 which are applied on a plane in which the electrophoresis gel is positioned, on either side of the gel. The feet 30 may slide on this plane.

FIG. 11: Top and bottom views of the mask holder which receives and maintains the mask by means of notches 43 and springs 28. The mask holder comprises a bearing zone 46 on which a pressure is applied to move the mask into contact with the gel.

FIG. 12: assembly of a carriage and a mask holder which are connected by two spring leaves 47 maintained by rivets 48. This assembly, when mounted on the guide rail 14 by the slide 49, permits to maintain the mask parallel to the gel and at the vicinity of the gel without contact.

Figure 1:
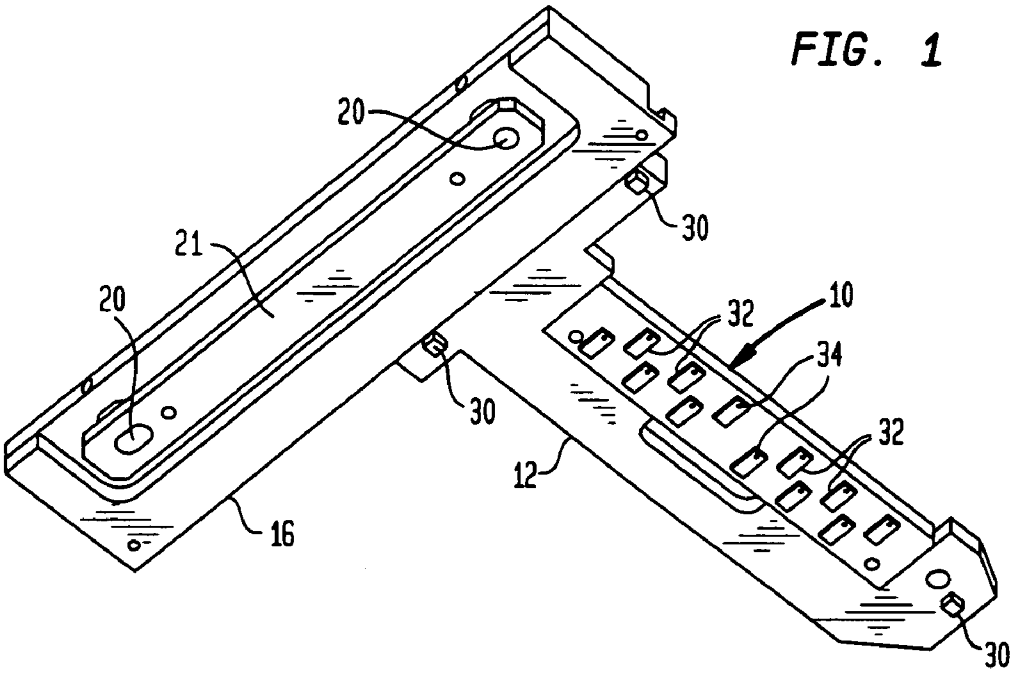
FIG. 1 is a diagrammatic perspective view from below of a mask holder device of the invention.

In order that the reagents loaded in the mask wells may descent, a pressure is applied on the mask holder. This causes a bending of the spring leaves 47 and the lowest part of the lanes, where the lower orifice of the filling conduits 34 is situated, comes into contact with the gel (an abutment system permits to limit the bending in order not to damage the gel). By releasing the pressure at the bearing zone 46, the mask is allowed to move up and returns to its initial position and the reagents contained in the conduits 36 are distributed by capillarity between the lower part of the lanes and the gel.

The mask is then moved forth and back by means of the handle 26.

Figure 13:
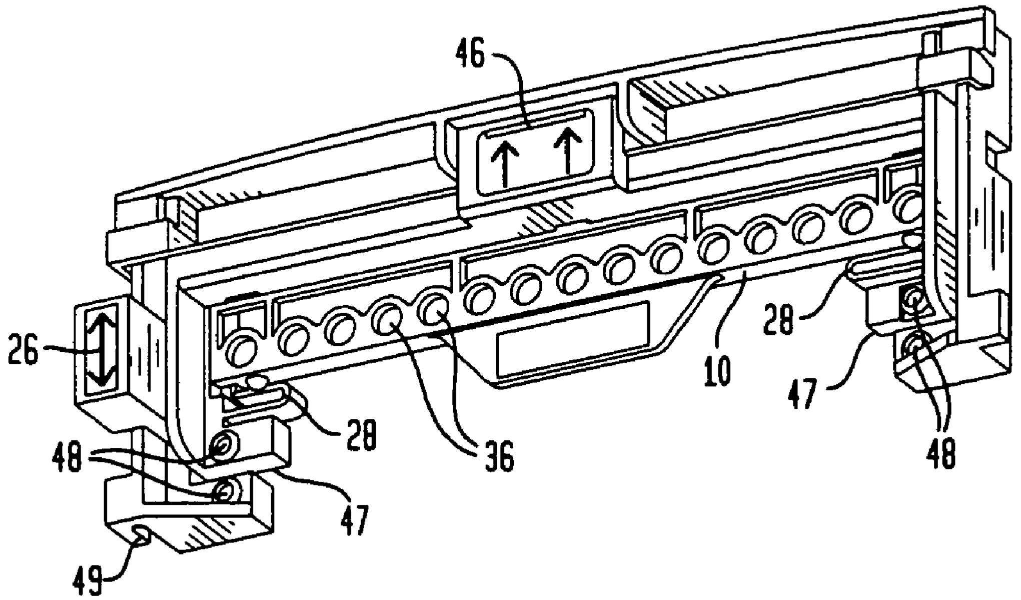

FIG. 13: Top view of the assembly comprising the carriage, the mask holder and the mask.

Figure 14:
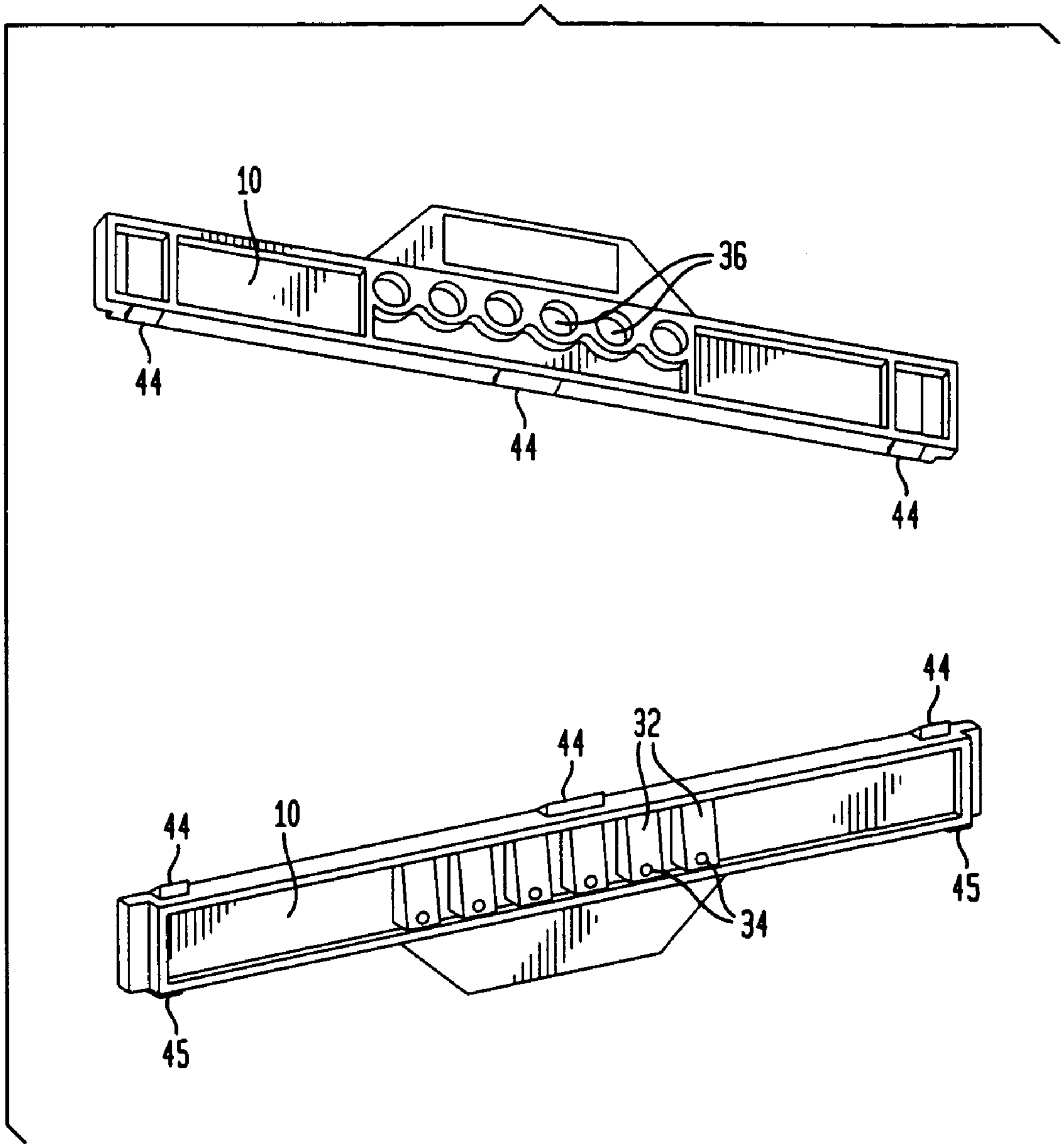

FIG. 14 represents the mask and guide assembly mounted on the positioning bar 50 on the electrophoresis plate in its end sweep positions.

Figure 15:
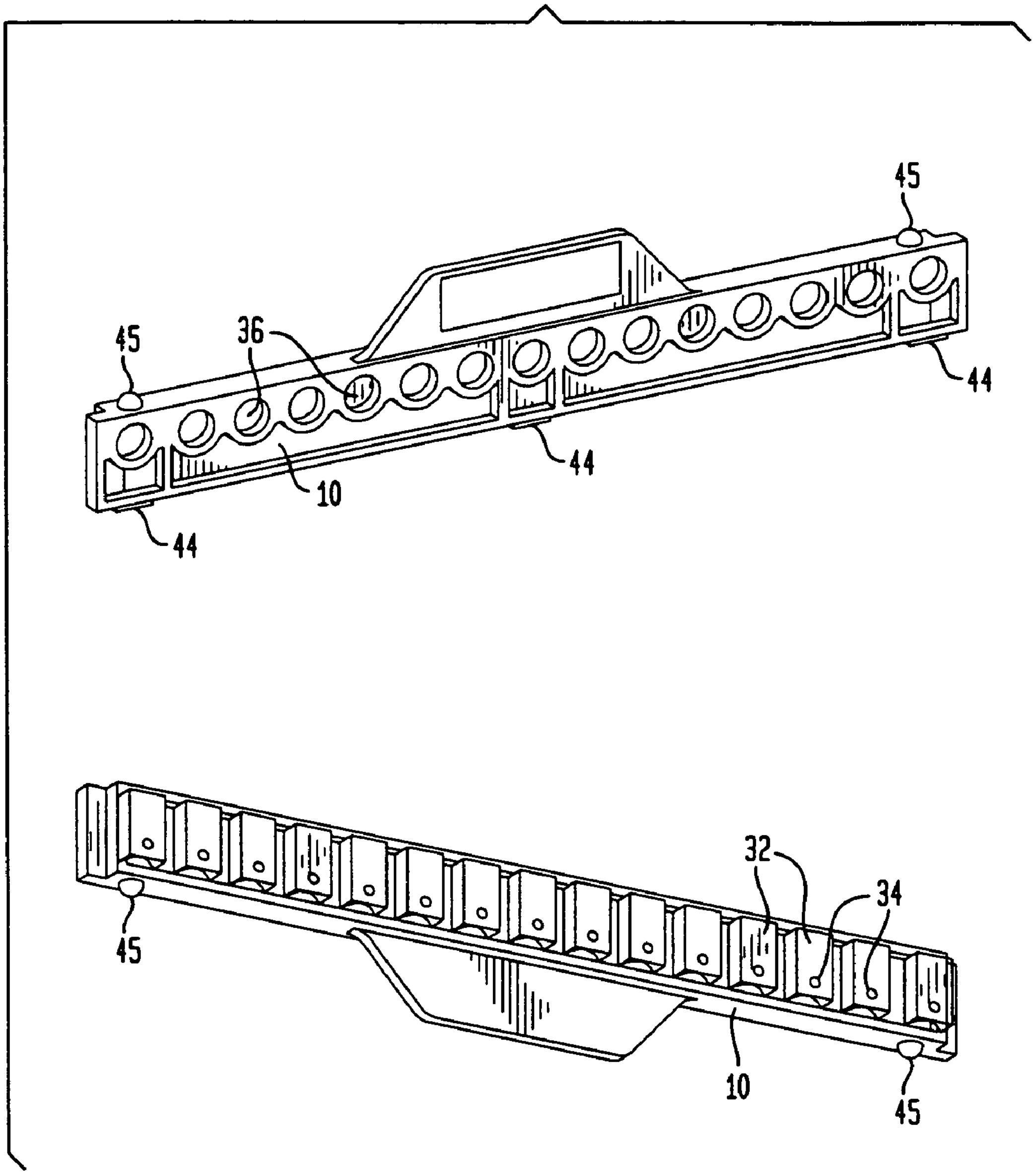

FIG. 15 represents the mask and guide assembly mounted on the positioning bar 50 on the electrophoresis plate in its end sweep positions.

Figure 16:
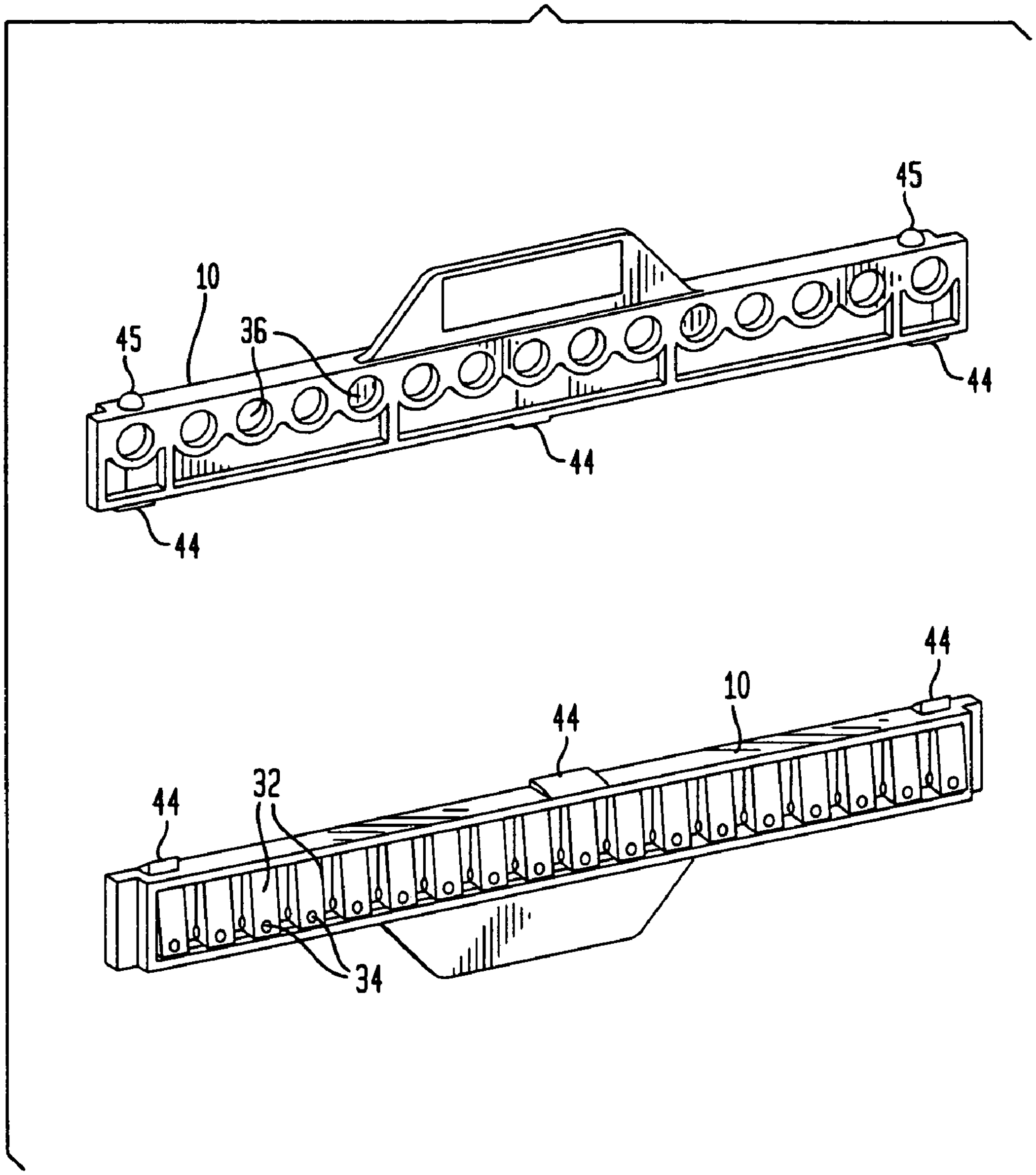

FIG. 16 represents the mask and guide assembly mounted on the positioning bar 50 on the electrophoresis plate in its end sweep positions.

Figure 17:
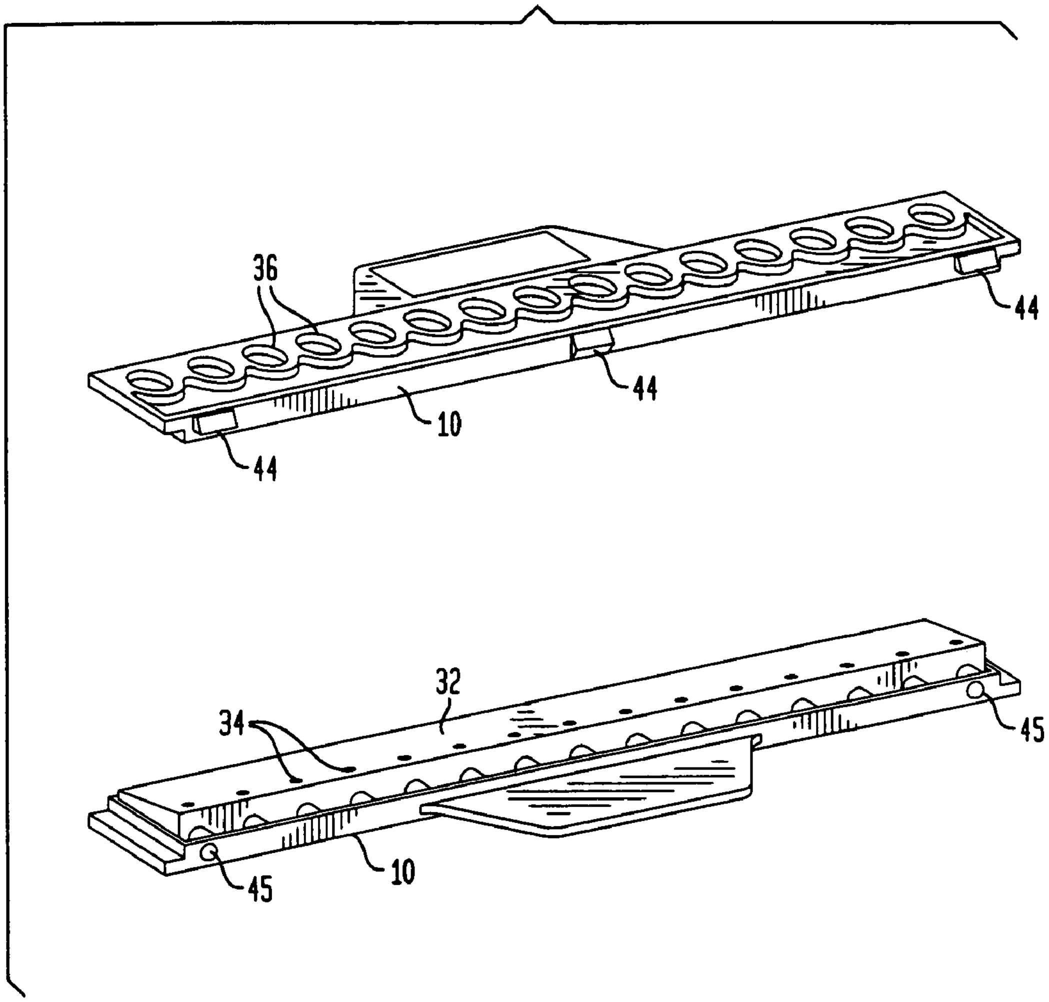

FIG. 17 represents the mask and guide assembly mounted on the positioning bar 50 on the electrophoresis plate in its end sweep positions.

Figure 18:
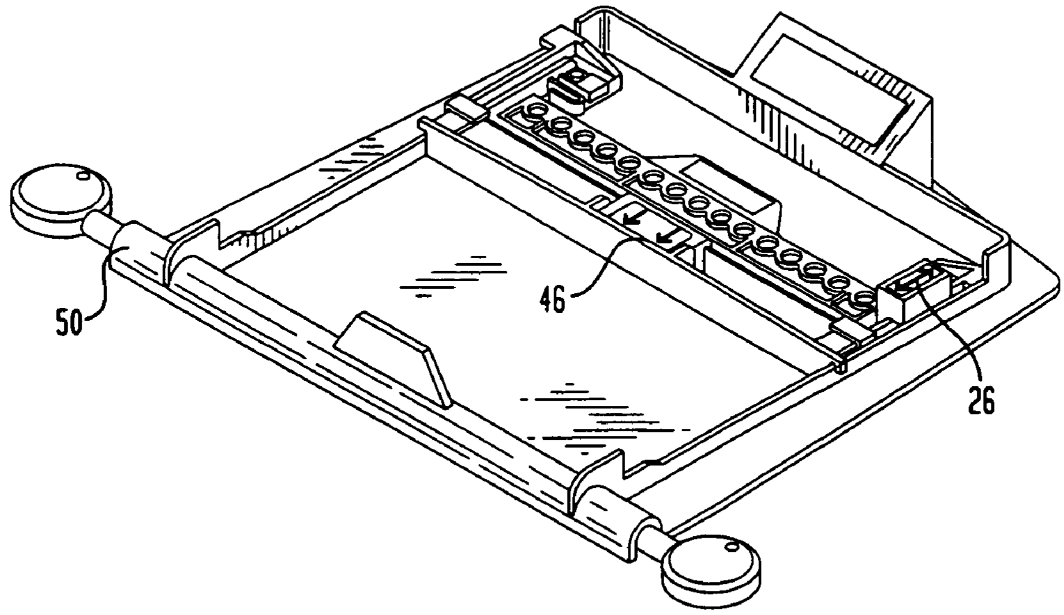
Figure 18:
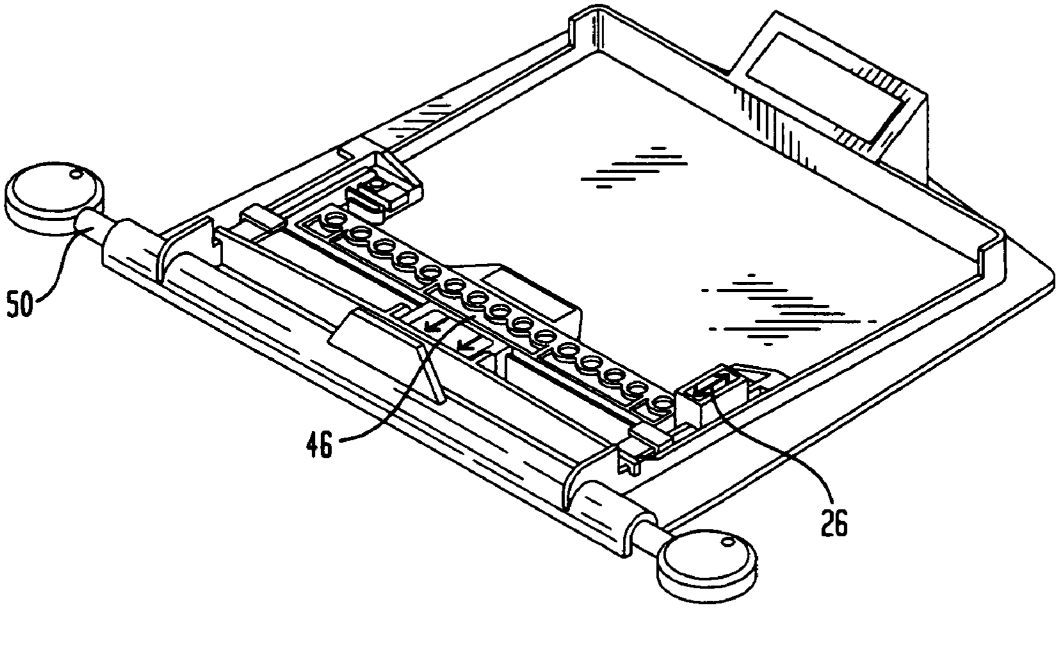

FIG. 18 represents the mask and guide assembly mounted on the positioning bar 50 on the electrophoresis plate in its end sweep positions.

DETAILED DESCRIPTION OF THE INVENTION

The dimensions of the mask of the invention are such that it does not cover the whole surface of the analytical support on which the reagents loaded on the mask are deposited and distributed, when the mask is brought in proximity of the analytical support, for operation. The width of the mask (comprising the length of its lanes) is in particular inferior to the length of the electrophoretic migration lanes of the analytical support, since the length of the lanes of the mask is smaller than the length of the electrophoretic migration lanes of the analytical support. The distribution of the reagents on these lanes results thus from the displacement of the mask above the analytical support as disclosed hereafter, and from the moving of the reagents on said support which is permitted as a consequence of the structure of the lanes of the mask.

The mask of the invention is thus intended for displacement above the analytical support, in order to enable the distribution of the reagents.

The opening is stated to be "associated with each lane", which in the context of the present invention means that its lower orifice is located so as to supply the reagent loaded into the opening in the mask to the slope of the lane, to allow the reagent to be deposited on the analytical support and to hold it by capillary action between the support and the lane and to distribute it on the analytical support during displacement of the mask.

Said opening is, for example a hole, perpendicular to the upper surface of the mask, traversing the mask from one side to the other. The lower orifice of the opening is preferably located in the slope, in the proximity of the lowest point of the slope. By being located "in the proximity of" the lowest point—with respect to a horizontal plane—of the slope of the lane, the lower orifice of the opening enable to distribute the liquid reagent in the lane, as the reagent rises along the lane.

The upper orifice of the opening can be vertical to the lower orifice. Alternatively, it can be positioned along an inclined plane with respect to this vertical provided that it allows the reagent to be supplied to the lower orifice under conditions compatible with the deposit and distribution of this reagent on the analytical support.

Advantageously, an opening associated with a lane, constituted by a hole perpendicular to the upper surface of the mask and traversing it from side to side is formed by a circular orifice opening in the upper surface of the mask, which is extended by a truncated conical portion ending, for example, in a cylindrical portion opening into the lower surface of the mask, via an orifice located in the slope of the lane in the proximity of the lowest point of the slope. The presence of a cylindrical portion opening into the lower orifice can distribute the pressure that can, for example, be exerted by a pipette on the edges of the lower orifice when loading the reagents, thus improving the strength of the mask.

The truncated opening can also advantageously guide a filler pipette and provide a seal between the end of the pipette and the mask when injecting the reagent between the lane and the analytical support.

If necessary, the above opening can be modified in that the conical portion extends to the upper orifice of the opening via a cylindrical portion with a circular cross section.

According to a particular embodiment of the invention, the opening thus disclosed can also be such that the upper orifice is larger than the lower orifice of the opening, for instance its diameter of the upper orifice is larger than the diameter of the lower orifice if the orifices are circular one.

A particular mask as defined above that is suitable for distributing reagents on an analytical support for biological samples can be defined as comprising:

a lower surface and an upper surface that are at least partially mutually parallel, separated by a distance constituting the thickness of the mask;

one or more lanes each comprising a projecting element of elongate shape emerging beneath the lower surface of the mask, said projecting element comprising a portion constituting a slope with respect to a horizontal plane;

associated with each lane, an opening traversing the mask over the whole of its thickness from an upper orifice on the upper surface of the mask to a lower orifice, said lower orifice being located in the lane in the proximity of the lowest point of the slope of the lane;

the mask being such that the lane or lanes it comprises can hold reagents loaded into each opening and deposited on the analytical support by capillary action between the lane and the surface of the analytical support facing which the mask is to be placed.

The lanes of the mask are elongate in shape and can also be termed ramps. Their slopes are all inclined in the same direction.

Said slopes are intended to retain the reagents by capillary action as indicated above and to ensure that the reagent is brought at the lowest point of the slope in order to permit its distribution when the mask is displaced.

A further particularly preferred mask of the invention as defined above comprises:

a lower surface and an upper surface that are at least partially mutually parallel, separated by a distance constituting the thickness of the mask;

one or more lanes each comprising a projecting element emerging beneath the lower surface of the mask, constituted by a protuberance in the shape of a truncated parallelepiped, said projecting element comprising a portion constituting a slope with respect to a horizontal plane;

associated with each lane, an opening traversing the mask over the whole of its thickness from an upper orifice on the upper surface of the mask to a lower orifice, said lower orifice being located in the lane in the proximity of the lowest point of the slope of the lane;

the mask being such that the lane or lanes it comprises can hold reagents loaded into each opening and deposited on the analytical support by capillary action between the lane and the surface of the analytical support facing which the mask is to be placed.

When the projecting element is constituted by an element with an elongate shape or is constituted by a protuberance in the shape of a truncated parallelepiped, said projecting element has an upper surface coinciding with the portion of the lower surface of the mask from which it emerges, and a lower surface that is separate from the upper surface along at least one slope to the horizontal, the lowest point of said slope located in the proximity of said lower orifice of the opening of each lane being the point that is closest to the analytical support facing it and in the proximity of which it is brought when in the position of use.

The projecting element comprising a slope emerging from the lower face of the mask can advantageously allow deposition and distribution of reagents loaded into the mask by displacing the mask along a zone of the analytical support that comes to face the lane or lanes of the mask in a plane that is horizontal with respect to this support.

In a further embodiment of the invention, the mask is provided with one or more lanes each comprising a projecting element emerging beneath its lower surface, said projecting element including a hollow sphere the cavity of which is intended to receive a reagent, and the dimensions of which are adapted to the width of the zone of the analytical support that has to be covered by the reagent, said reagent being held in the sphere cavity by capillary action and distributed over the analytical support as the mask is displaced, via a hole formed in the sphere. Such a mask will also have the characteristics defined above for the projecting elements with an elongate shape.

In a particular embodiment of the invention, the lower and upper surfaces of the mask are completely parallel to each other, away from the zones constituting the lanes, namely away from the zones constituting the slopes of the lanes.

In the context of the embodiments of the invention described above, the slope coincides with the lane at each lane of the mask regardless of the shape of the projecting element.

Alternatively, the slope can extend over only a portion of the lane. As an example, the lane comprising the lower orifice at the lowest point of its slope can be extended beyond said slope, for example in a horizontal plane. In a further variation, the slope can be constituted by a plurality of slopes.

When a mask in accordance with the invention is used in association with a support for analyzing biological samples, for example an electrophoresis gel, this mask is brought "into the proximity of" the analytical support: this means that the mask does not come into contact with the zones of the support onto which the reagents are to be deposited and distributed (the reagent incubation zones) and that the reagent or reagents deposited on said support are held by capillary action between the lanes of the mask and said analytical support, which allows them to be distributed over the predetermined zones of this analytical support located facing the lanes of the mask during its displacement parallel to the analytical support, above that support. The above absence of contact is more specifically, in particular embodiments of the invention, an absence of contact which follows the initiation of the descend of the reagents to allow their deposit on the analytical support, this descent indeed involving, according to a particular embodiment of the invention, a brief contact with the analytical support, as described and illustrated hereafter.

The slope formed at the projecting element of each mask lane is such that its point said to be the lowest is the point that is closest to the horizontal plane constituted by the analytical support in the position of use. As a result, the point termed the highest point of the slope of said lane is the point furthest from the horizontal plane constituted by the analytical support in this operational position. The lower face of each lane of the mask facing the support is thus inclined with respect to the horizontal.

During distribution of the reagents deposited on the analytical support, the position of the lanes with respect to the horizontal plane of the analytical support and the position of the lower orifice of the opening associated with each lane ensures that the reagents reach the lowest point of the slope of the lane, as at that point, the capillary forces exerted on the reagents are at their greatest.

The liquid constituting the reagent can be distributed over the whole of the lane or over only a portion of the lane.

The reagent or reagents can be deposited or distributed using the mask of the invention in a controlled manner over the delimited zones of the analytical support without establishing any contact between the lanes of the mask and the analytical support.

Away from the zones of the analytical support that come into line with the lanes of the mask during use, contact can be established between the mask and the analytical support since on moving, the mask can slide parallel to the analytical support along this support without damaging it.

In one particular embodiment of the invention, no point of the mask comes into contact with the analytical support during use, with the possible exception of zones of the mask that allow it to be positioned in the proximity of the analytical support.

Preferably, when the mask has to be supported to position it in the proximity of the analytical support, this is accomplished away from said analytical support, for example on the plane (or plate) on which the support is deposited.

When considering the upper surface and the lower surface of the mask, of the lanes or the slopes, these notions are considered to be made with reference to the position of the mask above an analytical support that is itself in the horizontal position. In other words, the lower surface of the mask and the lower surface of each lane or each slope are facing the surface of the analytical support when the mask is in the position of use. The horizontal plane with respect to which the slope of the projecting element is defined can thus be that of the analytical support when it is used in a horizontal position.

The invention also concerns a mask the use of which to deposit and distribute reagents on an analytical support calls on the principle of the invention, namely holding the reagents by capillary action between a slope defined in the mask and a zone of the analytical support facing said lane, said mask being distinguished from the mask defined above in that the slope constituted in each lane of the mask is produced by the inclination conferred on the mask with respect to the analytical support during its use. The lower surface of the mask in this case is parallel to the lower surface of the projecting element which comes to face the analytical support, the slope resulting from the inclined position of the mask with respect to the analytical support.

In the context of this particular embodiment, the characteristics of the lanes defined for masks wherein the slope is integrated into the lane are transposable when the slope is constituted by using the mask in an inclined position with respect to the analytical support.

When the lane is elongate in shape, it can have a parallelepipedal shape, its shape delimiting the zone for holding the reagents by capillary action between the lane and the analytical support. When in use, the opening traversing the mask is located at a point on the lane that is in the proximity of the lowest point of the slope formed by the relative inclination of the mask with respect to the analytical support.

The mask of the invention has dimensions that are compatible with the dimensions of the analytical support on which the reagents are to be deposited and distributed and the lanes of this mask have shapes and dimensions that are compatible with the volume of the liquid reagent that is to be deposited and distributed on the analytical support and with the shape and the dimensions of the delimited zones on the analytical support on which said reagents are to be deposited and distributed, for example with a view to their incubation with the constituents of the biological sample.

To deposit and distribute one or more reagents on the biological sample analytical support when the mask and the analytical support are disposed parallel to each other, the mask is displaced in a horizontal plane above the plane of the analytical support from the zone of the analytical support at the level of which the mask is initially positioned and which corresponds to the initial deposition point of the reagents, to distribute the reagents on the zones of the analytical support coming to face the lanes of the mask.

To deposit and distribute one or more reagents on the sample analytical support, when the slope of the lanes of the masks does not result from the structure of the lanes but from the inclination endowed on the mask with respect to the analytical support (or vice versa), the mask is displaced in a given inclined plane employing features that are identical to those described for the mask in which the lanes comprise a slope in their structure.

Each displacement permitting passage of the mask above the totality of the delimited zones of the analytical support that are to receive the reagents is termed a "sweep". A first sweep can, for example, be carried out from the zone corresponding to the anode of an electrophoresis support towards the zone corresponding to the cathode of such a support, or in the opposite direction from the cathode to the anode, to cover the whole of the delimited zones that have to receive the reagents, these zones corresponding to the electrophoretic migration lanes in the case of an electrophoresis support (such as a gel). In the following paragraphs, according to the above indications, when the anode is referred to in order to locate the deposit of the reagent or the moving direction of the mask with respect to the analytical support, it must be understood that this location or this movement can, opposite, be performed starting from the cathode.

During its displacement by sweeping the predetermined surface of the analytical support after loading the reagents into the opening associated with each lane, the mask of the invention can thus deposit and distribute said reagents over the totality of the predetermined zones on the analytical support for all of the test biological samples found in the direction of displacement of the mask.

Thus, it becomes unnecessary to multiply pipetting of each reagent for each sample to be treated. The number of pipetting operations to be carried out corresponds to the number of reagents that have to be deposited over one row of the analytical support and thus normally corresponds to the number of openings provided in the mask when all of the lanes of the mask are used.

Further, the quantity of each reagent loaded into the mask can be considerably reduced compared with the quantity of each reagent normally used when each reagent has to be loaded for each of the samples present on the analytical support.

By way of example, if the mask of the invention is intended to deposit and distribute reagents to carry out immunofixation to detect particular constituents of a biological sample that has already been analyzed by electrophoresis, when using 6 reagents for each test sample (i.e., generally a fixative that is capable of fixing the constituents of the sample to produce a reference profile on the electrophoresis support, and specific anti-IgG, IgA, IgM, κ and λ antiserums), the quantity of each reagent loaded into the mask is reduced by 4.5 times compared with the quantity loaded for each sample to be treated when using a fixed mask such as that described in EP-B1-0 526 271.

The quantity of each reagent loaded onto each lane of the mask is determined as a function of the dimensions of the incubation zone to be covered using this reagent, for example as a function of the number of rows of samples found in the direction of displacement of the mask. When the mask is used to deposit and distribute reagents for immunofixation, the incubation zone comprises or coincides with the zone of the electrophoresis support that comprises the electrophoretic profile for the samples to be analyzed.

By way of example, a mask comprising three groups of six lanes over a row can be used to carry out immunofixation of nine samples, or even 12 or 18 samples (distributed, for example, in rows of 3 different samples, each sample occupying 6 lanes of the analytical support for electrophoresis and thus of the mask).

The mask is advantageously loaded with a quantity of reagents such that each predetermined zone on the analytical support on which the reagent has to be distributed is already homogeneously covered with that reagent, in one sweep. To determine the loaded volume of each reagent, we take into account the path of the mask per sweep of the analytical support and of the width of the zone to be covered on the analytical support. Generally, the quantity of each loaded reagent varies between 4 μl and 15 μl, and is a quantity of 15, 10, 8, 6 or 4 μl per reagent, for example.

By way of example, we observe that a volume of 4 μl of reagent is sufficient to cover an analytical support surface of 175 $mm^2$, in a homogeneous manner, corresponding to a distribution of reagent of 0.02 $\mu l/mm^2$ of analytical support.

Preferably, the mask of the invention is a rigid mask, or stiffened by association with stiffening means which can, for example, participate in positioning and/or guiding the mask.

The choice of material used to produce the mask is not limited in principle.

The mask can, for example, be produced from a material that can be moulded to produce a smooth surface, in particular a plastic material.

The material may be transparent or translucent; examples are materials such as polycarbonate, polymethacrylate, polyethylene, crystalline polystyrene, and Plexiglas.

The mask of the invention can be disposable.

The stiffness conferred on the mask can allow it to be displaced in a predetermined plane, which may be horizontal or inclined, with respect to the analytical support, when associated, for example snap fitted, into suitable positioning means and appropriate guide means.

In a preferred embodiment of the invention, a mask with the characteristics defined in the foregoing pages comprises a plurality of mutually parallel lanes distributed over the length of the mask.

When, as is most frequently the case, the mask comprises a plurality of mutually parallel lanes, the distance between the lanes (inter-lane distance) is determined as a function of the number of lanes on the mask, and the necessity of preventing any interactions between the reagents, in particular between the fixative and the antiserums.

Advantageously, the distance between the different parallel lanes is constant. This distance can be small, for example less than 3 mm, in particular of the order of 2.5 mm, preferably 2 mm or more, in particular to prevent any interaction between the fixative and the antiserum of the neighboring lane.

The width of the zone of the analytical support at which distribution of each of the reagents has occurred is at least equal to the width of the mask lane brought to face that zone.

By way of example, the width of the lane and the width of the incubation surface, which can correspond with the distribution of the electrophoretic profile on the analytical support, are similar and about 2.5 mm. In a further example, the width in question is 3.5 mm.

To prevent an interaction between neighboring reagents, it is also possible to dispose the lanes of the mask to prevent overlapping of the different zones for depositing the reagents or of any possible diffusion zones for the reagents deposited on the analytical support, or it is possible to carry out the loading of the reagents and their descent on the analytical support in such a way that a possible interaction is prevented. Some embodiments to enable loading and descent of the reagents are described hereafter, including for example but not necessarily, a loading step outside of the analytical support, which permits to avoid such type of interaction but permits to maintain the lanes parallel and aligned.

Regarding the above discusses interactions, it is appropriate in particular, to ensure that the reagent intended for producing the reference profile for each sample does not interact with the specific reagents (in particular antiserums), which could falsify detection of particular constituents of the sample.

To this end, when specific means are present in the structure of the mask, a first embodiment of the mask comprising a plurality of mutually parallel lanes distributed over the length of the mask with a constant spacing consists of providing a first series of mutually parallel lanes distributed over the length of the mask and a second series of mutually parallel lanes that are parallel to the first series of lanes and wherein the lower orifices are located in the same horizontal plane, this second series of lanes forming an alignment that is offset with respect to the alignment formed by the first series of lanes.

In a variation of the mask, the offset alignment of the second series of lanes is replaced by increasing the spacing between said lanes of said first series and the other lanes of said second series.

The offset of the second series of lanes or the spacing of this series of lanes compared with the lanes of the first series is intended to prevent interaction between the reagents of the second series of lanes and those of the other lanes during deposition onto the analytical support. In general, these offset lanes or more spaced lanes are intended to receive a fixative for immunofixation, capable of fixing proteins of the electrophoretic profile to produce a reference profile.

When the mask does not contain a series of offset lanes or a series having a different spacing compared with that of the other lanes, the interaction between the reagents in question can be avoided, if necessary and for example, by carrying out loading and deposition of these reagents onto the analytical support separately in two sweeps.

As an example, the fixative is deposited on the anode side of the electrophoresis support, then distributed by sweeping before loading with the antiserums, for example in the anodic but offset position, for example about 5 mm further towards the cathode with respect to the position of the first loading run. Alternatively, the antiserums can be loaded onto the cathode position.

Having recourse to a two-stage loading is however not always required, especially when the loading procedure of the reagent does not lead to a disturbing interaction between the reagents. Such interaction can, for example, be prevented even if all the reagents are loaded simultaneously outside of the surface of the analytical support and when the simultaneous descent of all the reagents can be performed on the analytical support without creating a disturbing interaction.

When the mask is produced so that the slope of the lanes results from the inclination of the mask with respect to the analytical support and not from the structure of the lanes, the offset of the lanes or groups of lanes is not necessary, and the reagents can then be loaded and deposited in several stages depending on their nature.

The mask of the invention can be produced so that the lanes are organized into a plurality of groups, each group, for example, being constituted by a lane positioned in an offset manner with respect to the other lanes aligned with respect to each other, and by the aligned lanes preceding the next offset lane.

Further, the mask of the invention is such that its structure, and if necessary the conditions of its use, allow the deposition and distribution of the reagents without interaction between the different reagents deposited on the different zones of the analytical support.

In particular for the zone for initial deposit of the reagents onto the analytical support, it has been observed that prior to their distribution, there is a localized diffusion phenomenon of said reagents on the analytical support.

To avoid any consequences of localized diffusion phenomena regarding the reagents on their deposition, it is advantageous to choose to deposit reagents with a mask away from the zone of the analytical support that is susceptible of carrying the constituents of the samples to be detected, thus for example away from the zone comprising the electrophoretic profiles.

In the case of immunofixation, said reagents are, for example, deposited in a zone located away from that corresponding to the electrophoretic profile, for example on the anode side of the support with respect to these profiles.

Advantageously, the mask of the invention is such that the opening traversing it from one side to the other is perpendicular to the upper and lower surfaces of the mask.

The shape of the openings of the mask must allow a sufficient quantity of reagents to be deposited therein to allow deposition and distribution of this reagent over the whole of the predetermined zone of the analytical support without having to reload the mask with said reagent.

Further, the shape and location of this opening is compatible with depositing and holding by capillary action a given quantity of reagent between the lane of the mask and the analytical support, until the quantity introduced during the operation for distributing the reagent on the analytical support is exhausted.

When depositing reagents on the analytical support, when the mask is loaded above the analytical support with the filling of the lanes being carried out as the reagents are loaded, it is appropriate to provide a seal between the mask and the end of the pipette or any other means used to load the reagents into the mask.

The volume of the opening can be designed to allow loading of the reagents externally of the analytical support, the reagents in this case having to be retained by capillary action in the opening in their entirety, until they are deposited on the analytical support. In this case, the mask is then positioned to ensure deposition of the reagents it contains, on the analytical support. This positioning must thus ensure that contact is established between the liquid and the analytical support, possibly using particular features.

Advantageously, in each lane, the opening can receive the excess reagent over the quantity of reagent required for the reaction.

The mask of the invention can employ reduced quantities of reagents, for example about 15 Ξl or 10 µl. However, the dimensions of the opening traversing the mask and intended to receive these reagents can be determined to allow a quantity of reagents that is higher than the effective quantity employed to be accepted. As an example, the volume of the opening can accept a quantity of reagent of up to about 30 μl.

The geometrical characteristics of the mask, in particular the number of lanes and the distance between the lanes (inter-lane distance) are adapted to the number of deposits, to their width and to the spacing of these deposits, formed in rows on the analytical support. The mask of the invention has thus a sufficient length to comprise several lanes formed in a row, and a limited width (smaller) with respect to the length of the electrophoretic migration lane of the incubation surface of the analytical support facing this lane when the mask is displaced when operated.

It is understood, and this constitutes a characteristic of the present device, that the same mask can be used to produce a plurality of rows of deposits with the same number and dimensional characteristics on the same gel. These rows of deposits have been produced on the analytical support in rows that are mutually parallel, and perpendicular to the direction of electrophoretic migration.

Advantageously, the geometry of the mask of the invention allows deposition and holds the reagent by capillary action between each lane of the mask and the analytical support, when the distance between the mask and the analytical support is 2 mm or less, preferably in the range 0.1 to 1.5 mm. This distance between the mask and the analytical support varies depending on the point on the mask under consideration; in particular, this distance is preferably about 0.1 to 0.5 mm at the point on the mask that is closest to the support (corresponding to the lowest point on the slope of the lane or the slope of the mask) and this distance is preferably less than 2 mm, advantageously less than 1.5 mm or less, at the point on the mask that is furthest from the analytical support (corresponding to the highest point of the slope of the lane or the slope of the mask).

Within these limits, the inclination of the slope must be such that the spacing of the mask from the analytical support is compatible with the capillary forces that maintain the reagent between the lane and the analytical support.

By way of example, a mask of the invention is produced so that the lanes are separated from each other by a distance of 1.5 mm or more. Preferably, the distance between the lanes is 2.5 mm. The lane width is advantageously 2.5 mm.

The mask lane reserved for the fixative can also be offset; for example, it can be in a position that is closer to the anode than the other lanes, when the mask is in the position of use, in the proximity of an analytical support constituted by an electrophoresis gel.

A particular mask is characterized in that the lane intended for fixative is not aligned with the other lanes and is offset compared with the alignment formed by the others, by a distance of 5 mm, preferably 6 to 7 mm.

A particular mask that is suitable for the invention, and in particular a mask that is suitable for use with a 10 cm long electrophoresis gel and with a width (between the anode and cathode poles) of about 8 cm is such that each lane of the mask has the following dimensions:

length: 3 to 15 mm;

width: 1 to 10 mm;

inclination of the slope: 1° to 10° to the horizontal.

A particularly preferred mask that is suitable for use with the above gel is a mask in which each lane has the following dimensions:

length: 7 mm;

width: 2.5 mm;

inclination of the slope: 5° to the horizontal.

In these particular embodiments, the other characteristics of the mask described above can, naturally, be associated with the particular characteristics given above. In particular, the inter-lane distance is advantageously 2.5 mm and/or the offset between the alignment of the lanes for the specific reagents and the alignment of the lanes for the fixative is 6 to 7 mm.

Again, in a particularly advantageous embodiment of the invention, the mask is such that the opening that traverses it having the characteristics given above in that regard has a conical portion forming an angle of about 50°.

In the context of the different embodiments of the invention, the thickness of the mask is advantageously in the range 1 to 10 mm.

When the mask of the invention is used to deposit and distribute the reagents on the electrophoresis support, it can again be characterized in that it is compatible with the characteristics of localization of the biological samples separated on the electrophoresis support; in particular, said mask can:

align the rows of lanes on the mask, perpendicular to the direction of electrophoretic migration;

position the mask in the proximity of the analytical support, to hold the reagents by capillary action between the lanes of the mask and the analytical support;

position the mask transversely with respect to the direction of electrophoretic migration to allow the alignment of the rows of the electrophoretic migration carried out on the analytical support with the rows of the mask lanes.

For use with different analytical supports, and by way of example, a mask in accordance with the invention can comprise in the range 1 to 24 lanes, preferably in the range 6 to 24 lanes, in particular 6, 9, 12, 15 or 18 lanes.

If intended for use in an immunofixation reaction following electrophoretic separation, a mask comprising 18 lanes can deposit, for three different samples occupying the same row of the electrophoresis support, and for a given number of rows of samples (for example 2 or more, in particular 3 or 4), a fixative to produce a reference profile and 5 specific reagents such as antiserums, in particular anti-IgG, anti-IgA, anti-IgM, anti-κ and anti-λ, for each sample. It is also possible to produce a mask with 6 or 12 lanes using the same features.

The invention also concerns a mask as defined above, associated with positioning means intended to hold the lower surface of the lanes of the mask in the proximity of the surface of the analytical support close to which the mask will be brought to deposit and distribute the reagents on the analytical support.

Suitable positioning means can be constituted by abutments that can rest on the analytical support away from the incubation surface comprising the biological samples, the dimensions of these abutments being such that the mask does not come into contact with the analytical support over its portion corresponding to the incubation surface of the reagents.

The positioning means can also be associated with means for guiding the mask to allow it to be displaced in a controlled manner above the analytical support, in accordance with the foregoing.

Thus, in a further aspect, the invention provides a device for depositing and distributing one or more reagents on an analytical support for biological samples, comprising:

a mask as defined above;

means for positioning and guiding the mask allowing the mask to be positioned so that the mask is held in the proximity of the surface of the analytical support and allowing the mask to be guided by sweeping the surface of the analytical support, in a horizontal plane parallel to the surface of said support, to allow to deposit and distribute the reagents over each of the determined zones of the analytical support coming into line with the lanes of the mask.

In a variation of the invention, the mask used is such that the slope of the lanes results from the inclination of the mask with respect to the analytical support. In this case, the invention provides a device for depositing and distributing one or more reagents on an analytical support for biological samples, comprising:

a mask as defined above;

means for positioning and guiding the mask allowing the mask to be positioned so that the mask is held in the proximity of the surface of the analytical support and allowing the mask to be guided by sweeping the surface of the analytical support, in a determined plane inclined to the surface of said support, to allow to deposit and distribute the reagents over each of the determined zones of the analytical support coming into line with the lanes of the mask.

In a particular embodiment of the invention, the device defined above is such that the means for positioning and guiding the mask can establish a distance between the analytical support and the point on the mask that is closest to said support (corresponding to the lowest point of the slope) that is in the range 0.1 mm to 0.5 mm, and a distance of less than 2 mm, preferably 1.5 mm or less, from the point furthest from the mask and the support (corresponding to the highest point of the slope).

The distance between the analytical support and the point on the mask that is closest to said support is preferably 0.5 mm.

The means for positioning and guiding the mask of the invention can be any suitable means, if appropriate present in an electrophoresis instrument. A course limiter can, for example, be an abutment.

The guide means advantageously comprise a course limiter to delimit the mask displacement course.

In one particular embodiment of the invention, the positioning and guiding means can allow automated displacement of the mask along the analytical support. However, the mask of the invention can readily be manually displaced, to cover the whole of the determined zones on the analytical support with the reagents contained in the mask by sweeping, if appropriate by means of a plurality of outward-and-return displacements.

The invention also concerns a method for depositing and distributing one or more reagents on an analytical support comprising biological samples, the method comprising the steps of:

positioning a mask as hereinbefore defined or a device as defined above in the proximity of the analytical support;

loading the reagent or reagents onto the mask to deposit the reagent or reagents onto the analytical support, holding them between said support and the lanes of said mask by capillary action;

displacing the mask by sweeping the analytical support to allow distribution of the reagent or reagents on the analytical support into the delimited zones of said support, the reagent or reagents being distributed in a quantity sufficient to allow their interaction with the constituents of the biological samples present on said analytical support.

When the lanes of the mask comprise a sloped portion, the mask is displaced in a horizontal plane with respect to the plane of the analytical support above the support and parallel to the support.

When the lanes of the mask do not comprise a slope and are therefore positioned in an inclined manner with respect to the analytical support to produce the slope, the mask is displaced parallel to the plane of the analytical support that is itself in the horizontal position if the mask is inclined.

When the mask is positioned in the proximity of the analytical support, and as soon as the reagents come into contact with the analytical support, it can be displaced immediately by sweeping above said analytical support.

When the reagents are distributed over the determined zones of the analytical support, for example over zones corresponding to the electrophoretic migration lanes of the biological samples, these zones constitute the incubation zones for said reagents with the constituents of the samples.

One advantage of using the mask of the invention lies in the fact that when distribution is terminated, the mask can immediately be removed from the delimited zones constituting the incubation zones of the analytical support, the quantity of reagent loaded into the mask having been exhausted.

One further advantage linked to the use of the mask of the invention is to allow uniform distribution of the reagents over the incubation zones.

Advantageously, an excess quantity of reagent is used with respect to the quantity required to cover the zones of the analytical support where incubation between the constituents of the samples and the reagents takes place. An excess of reagent is a quantity more than that distributed by a single passage (one sweep) at a sweep rate over the analytical support of about 2 cm/s.

The quantity of reagent left on the analytical support per unit area of swept surface depends on the surface area and in particular on the sweep length. It rises as the sweep rate reduces.

The rate of displacement of the mask with respect to the analytical support is normally in the range 0.5 to 2 cm/s.

By way of example, to distribute the reagents on an electrophoresis support with a width of 8 cm determined between the anode and cathode (corresponding to the sweep length), two displacements each comprising an outward and a return trip can be carried out, each displacement taking about 3 seconds. In this case, a quantity of reagent per lane in the range 6 μl to 10 μl can be deposited.

At slow rates, i.e., at about 0.5 cm/s, and for a lane width of 2.5 mm, a reagent in a quantity of 3–4 μl introduced beneath the lane will be exhausted after a path of 70 mm.

For 2.5 mm wide lanes and with a sweep path for the mask of 70 mm compared with the analytical support, the volume of reagent advantageously employed is about 8 to 10 μl/lane.

When the first sweep has been carried out, some reagent is left under the lane even if the displacement is slow, at 0.5 cm/s, and especially if the displacement is at an average rate of 2 cm/s.

Other sweeps will be necessary to completely exhaust the reagents introduced. The number of sweeps can vary as a function of the volume of reagent introduced into each lane.

In practice, the volume of each reagent employed is such that 4 sweeps are sufficient to exhaust the reagent.

With 10 μl loaded into each opening, the mask then, for example, undergoes 2 outward and return trips for a sweep length of 70 mm. Once all of the reagents have been distributed onto the surface after these 4 passes, the mask is withdrawn with no risk of unintentional distribution and the incubation phase proper is commenced.

According to a particular embodiment of the invention, two sweeps (one XXX outward-and-return displacement) to distribute the reagents on the analytical support. Even if after the sweeps, a small quantity of reagent remains on the analytical support, it is not necessary to remove it before incubation. The operating conditions of the mask enable a uniform distribution.

If the sweep length is reduced, the quantity of reagent distributed per lane is advantageously reduced.

We indicated above that the mask used to carry out the method for depositing and distributing one or more reagents on an analytical support is advantageously a mask in which the lanes intended for the fixative capable of fixing the constituents of the biological samples to produce a reference profile are offset with respect to the other lanes, as described above.

This offset between the fixative lane and, for example, the lanes intended for the specific antiserums, avoids an interaction between the reagents when being deposited on the analytical support. This offset is particularly justified when all of the reagents are loaded onto the mask and deposited together.

Alternatively, for example when the lanes intended for the fixative are not offset, the mask is loaded in two runs, to deposit firstly antiserums and then the fixative. This two-step loading can alternatively be carried out by initially loading and depositing the fixative then loading and depositing the specific reagents.

Alternatively also, the loading can be carried out in one step, if the conditions for the deposit of the reagents on the analytical support are such that they do not lead to interactions between the reagents, in particular between the specific reagents and the fixative if any.

When the mask is such that it has to be used in an inclined position to produce the slope in the lanes compared with the analytical support, the lanes are not offset from each other, but loading of reagents which must not be allowed to interact (for example, fixative and antiserums) is carried out in either in two stages: the initially loaded reagent is distributed by sweeping prior to loading the reagent (for example antiserum) loaded in a second stage, or in conditions allowing to avoid disturbing interactions when depositing the reagents on the analytical support.

In a particular implementation, the deposition and distribution method of the invention is carried out so as to load the mask with the reagents away from the zone of the surface of the analytical support comprising the biological samples.

When carrying out this loading, which takes a certain amount of time (30 seconds to 2 minutes), the zone of the analytical support covered by the reagents at this location is wider than the lane itself as a result of diffusion. This diffusion could cause abnormal enlargement of the profile, revealed after incubation of the reagent with the constituents of the biological sample, should this loading be carried out vertically to a zone comprising a profile of the constituents of the samples that are to be revealed.

If the mask is loaded away from the zones of the analytical support comprising the constituents of the samples, this disadvantage resulting from diffusion of the reagents from the deposition zone does not occur.

When the size of the surface of the analytical support allows it, said loading can be carried out in the anode portion beyond the zone in which the electrophoretic migration profiles for said samples are located. The loading can alternatively be carried out in the cathode portion beyond the zone in which the electrophoretic migration profiles for said samples.

When the size of the surface of the analytical support does not allow such deposition beyond the zone containing the sample electrophoretic migration profiles, the mask can be loaded outside the support surface, for example onto a thin sheet of plastic, this sheet coming into contact with the analytical support and in the plane of the surface of this support but extending beyond this surface.

The invention also concerns a method for depositing and distributing one or more reagents on an analytical support comprising biological samples, the method comprising the steps of:

loading the reagent or reagents onto the mask to allow the reagent or reagents to be deposited on the analytical support, and being held between said support and the lane or lanes of said mask by capillary action;

positioning a mask as hereinbefore defined or a device as hereinbefore defined in the proximity of the analytical support;

displacing the mask by sweeping the analytical support to distribute the reagent or reagents on the analytical support in delimited zones on said support, the reagent or reagents being distributed in a quantity sufficient to allow them to interact with the constituents of the biological samples present on said analytical support.

The features indicated above for carrying out the deposition and distribution method are applicable in this instance.

In this implementation of the mobile mask loaded prior to positioning it above the analytical support, all of the reagents have been introduced into the upper orifices of the openings associated with each lane of the mask, which then act as reservoirs. These reagents are held in them due to capillary action despite the presence of a lower orifice for each opening.

In the configurations described above, when the mask is loaded above the analytical support, the mask already having been placed at the required distance (about 0.5 mm for the lowest point) from said support, the reagents are introduced directly between the lanes of the mask and the analytical support.

To this end, during the phase for expelling the reagent that has been held in the tip of the pipette, a seal is provided between the end of this tip and the upper orifice of the mask, for example by holding the pipette in the vertical position with the tip bearing lightly against the bottom of the opening in the mask in the conical portion close to the lower orifice of the opening. When this lower conical portion is extended by a cylindrical portion, the diameter of this latter (for example 0.8 mm) does not allow passage of the pipette tip. This ensures "forced" expulsion of the reagent via the lower orifice of the opening associated with the lane, the droplet that beads out from this lower orifice coming into contact with the analytical support located in its proximity (0.5 mm) and distributing itself by capillary action between the lane and the support. When the pipette tip/upper orifice seal is not obtained, the reagent remains in the upper orifice and does not descend onto the analytical support.

This is precisely the case when the seal is provided but when the lower orifice is not in the proximity of the analytical support surface, i.e., when loading is carried out away from the analytical support.

Under these conditions, the droplet that has beaded out (but has not fallen because of its very small volume of 10 to 15 μl) and has remained attached by capillary action close to the lower orifice, rises into the well constituted by the upper orifice when the "tip/upper orifice contact" is destroyed by removing the pipette.

This particular implementation of the mask with loading prior to positioning it above the analytical support has the advantage of being capable of being carried out automatically, for example by means of the Hydraplus SEBIA automated instrument, removing the need for any manual pipetting and further simplifying loading of the mask.

The mask loaded with reagents distributed in the upper orifices acting as a reservoir can be kept in a moist chamber for a period of a few minutes to a few hours prior to use.

Different means can be envisaged for bringing the reagents loaded into the mask into deposition on the analytical support.

In a first embodiment, the mask and mask holder assembly (the mask holder constituting a means for positioning the mask) loaded with different reagents is positioned above the analytical support by attaching it to a guide rail and bringing it into abutment in the anode position. The mask assembly is covered with a small chamber (FIG. 3) covering all of the upper orifices and bearing on the periphery of the mask (a planar surface sealing against a planar surface). This chamber is provided with a fitting via which a small volume of air, 50 to 200 μl, is rapidly injected (for example using a syringe). This increase in pressure in the sealed chamber causes each of the reagents to bead out below the mask lanes and these reagents then touch the gel. Following this contact with the analytical support, they are simultaneously distributed between the lanes of the mask and the analytical support by capillary action. The surface of the analytical support is then swept.

In a further embodiment, the mask and mask holder assembly that has already been loaded is positioned above the analytical support by attaching the mask holder to the guide rail and is brought into abutment in the anode position.

The reagents can be caused to fall onto the analytical support from the upper orifices of the mask that act as a reservoir by introducing, vertically into each of the upper orifices, a cylindrical rod with a diameter that is lower than that of the lower orifice of the mask (for example 0.5 mm) constituted by a material with a hydrophilic nature (for example stainless steel) until the rod comes into contact with the analytical support.

This rod can establish a junction between the liquid introduced into the upper orifice and the analytical support. All of the liquid introduced then descends by capillary action along the rod and distributes itself between the lane and the analytical support.

The simultaneous descent of all of the reagents onto the analytical support can be achieved by introducing a rod into each of the upper orifices of the mask vertically and simultaneously, these rods of the same length (5 to 10 mm) being rendered integral with each other, for example by insertion into a rectangular Plexiglas plate with the same dimensions as the mask and with a geometry such that it exactly reproduces the disposition of the orifices of the mask. When all of the reagents have been distributed between the lanes of the mask and the analytical support, the Plexiglas plate provided with the rods is withdrawn and the mask is swept across the gel surface.

In a further implementation of the invention, a third method that allows all of the reagents to be dropped simultaneously onto the gel consists of providing it with a mechanical impulse, after positioning the mask in abutment (especially in anodic or in cathodic abutment) above the analytical support. This impulse can, for example, be obtained by snap fitting the loaded mask into the mask support.

This impulse can project a drop of reagent, until then held by capillary action in the reservoir of the mask, onto the analytical support by inertia, and thus establishes a junction between the lowest point of the mask lanes at the lower orifice of the lanes and the analytical support so that all of the reagents located in the reservoirs are distributed by capillary action between the mask lanes and the analytical support. The gel surface can then be swept.

In a still further implementation, when the mask is loaded away from the analytical support, after distributing the reagents into the upper orifices and installing the mask above the analytical support, the mask is briefly brought into contact with the analytical support at the lowest point of the slope of the lanes. The purpose of such contact is to allow all of the reagents to fall onto the analytical support before distribution is commenced.

Once the loaded mask is in the position of use in one of the above implementations, i.e., when each lane has received a predetermined quantity of reagent, the mask is displaced parallel to the analytical support in the direction of electrophoretic migration, using guide means. The result of this displacement is to entrain the liquid located between the lanes of the mask and the analytical support by sweeping the surface of the analytical support coming into line with the lanes of the mask. The liquid held between the mask and the analytical support by capillary action is entrained in particular due to the slope of the lanes which enable that the reagent be brought at its lowest point during the displacement and a certain quantity of reagent is then deposited on the analytical support into which it penetrates and remains. As sweeping progresses, the volume of liquid contained beneath the lane is consumed by penetration into the analytical support and reduces.

The invention also concerns a method for depositing and distributing reagents on an analytical support, in which the step for loading the mask with the reagent or reagents is automated.

In a further implementation of the invention, the step for displacing the mask for sweeping the analytical support is automated.

The method of the invention is advantageously carried out to detect biological sample constituents, previously separated by electrophoretic migration, this detection possibly involving immunofixation, the reagents in this case being specific antiserums and preferably a fixative to produce a reference electrophoretic profile.

Such a method of the invention can be carried out under the usual conditions for carrying out electrophoresis and immunofixation techniques. The reagents used are the usual reagents, but these reagents are advantageously being used in a quantity that is lower in the invention compared with the quantities normally employed.

The invention also provides a method for detecting the constituents of one or more biological samples by immunofixation, comprising:

carrying out electrophoresis of the biological sample or samples to separate out the constituents;

carrying out a method for depositing and distributing reagents on an electrophoresis support, preferably an agarose gel, in accordance with the invention;

incubating the biological samples separated by electrophoresis with the distributed reagent or reagents to allow immunofixation.

Such a detection method can also be characterized in that it further comprises a step for revealing the constituents of immunofixed biological samples and if appropriate, a step for quantifying the revealed constituents.

These revealing and quantification steps can be carried out using any known means.

Advantageously, in the context of the invention, the methods defined above can simultaneously analyze 3n, 2n or n biological samples respectively, n being a whole number representing the number of rows of deposits, using a mask with 18, 12 or 6 analytical lanes respectively. Preferably, n is 2, 3 or 4.

However, in principle, there is no limit to the number of lanes on the mask.

Because of the structure of the mask and the features of its use, the quantity of each reagent loaded onto each lane of the mask, i.e., introduced into each opening of each lane and held by capillary action beneath each lane, can advantageously be reduced, and is, for example, less than 15 μl/lane. Preferably, the quantity is 10 μl/lane or less.

When the reagents are deposited on the analytical support, they are in the liquid form. Thus, the invention concerns the use of liquid reagents to load the mask. The invention also concerns the use of a mask loaded with liquid reagents, the mask then being freeze dried so that the reagents contained in the openings of the mask are freeze dried until the mask is used when the reagents are in the form of solutions for the deposition step.

In a further aspect, the invention provides a kit comprising:

at least one mask as defined above;

at least one analytical support, in particular an electrophoresis support.

Such a kit can also comprise:

reagents for immunofixation of the constituents of samples separated by electrophoresis;

a fixative for fixing each sample of the ensemble of constituents separated by electrophoresis.

The kit can also comprise at least one comb for depositing samples on the analytical support.

If the mask has to be loaded away from the electrophoresis support, the kit can comprise means, for example as described above, to cause the reagents to fall from the openings in the mask onto the analytical support.

Such a kit is preferably suitable for simultaneous separation of 9 or even 12 samples on each electrophoresis support, using a mask with 18 lanes.

Preferably, such a kit can allow simultaneous separation of 18 samples on each electrophoresis support.

A kit in accordance with the invention can also contain indications relating to the use of the mask of the invention, for example in the form of instructions for use including information regarding the quantities of reagents to be loaded onto the mask and/or on the conditions for displacing the mask, such as the sweep rate or the recommended number of sweeps.

If need be, according to a particular embodiment of the kit of the invention, the mask is not with the analytical support which can be obtained independently.

The mask of the invention can advantageously be loaded with the reagents.

Further, the invention concerns an electrophoresis support for separating at least 9 biological samples disposed in 3 rows of 3 samples, for immunofixation, said support comprising at least 18 migration lanes, said lanes being spaced from each other by a distance of 2 mm and being 3 mm wide, and the total length of the migration lanes being at most 63 mm.

Figure 2:
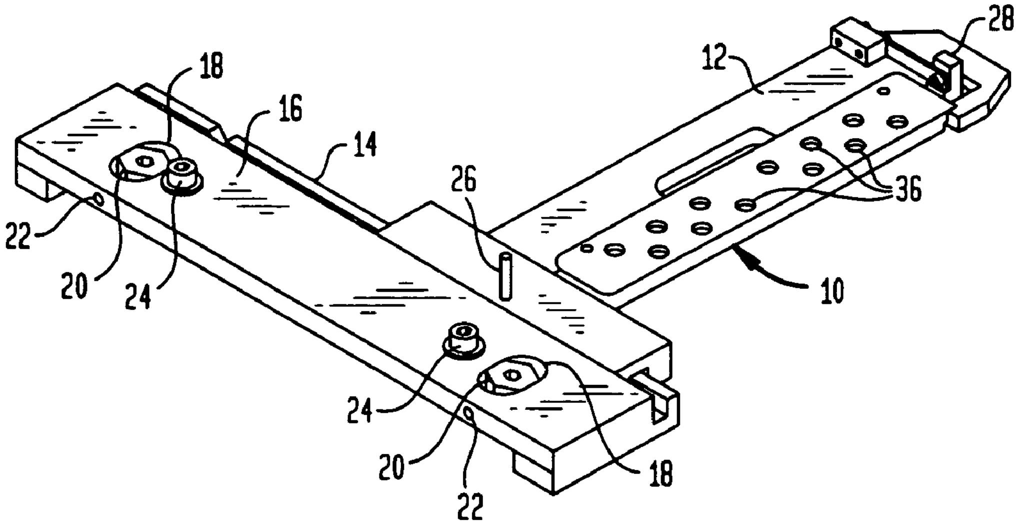
FIG. 2 is a diagrammatic perspective top view of this device.
Figure 3:
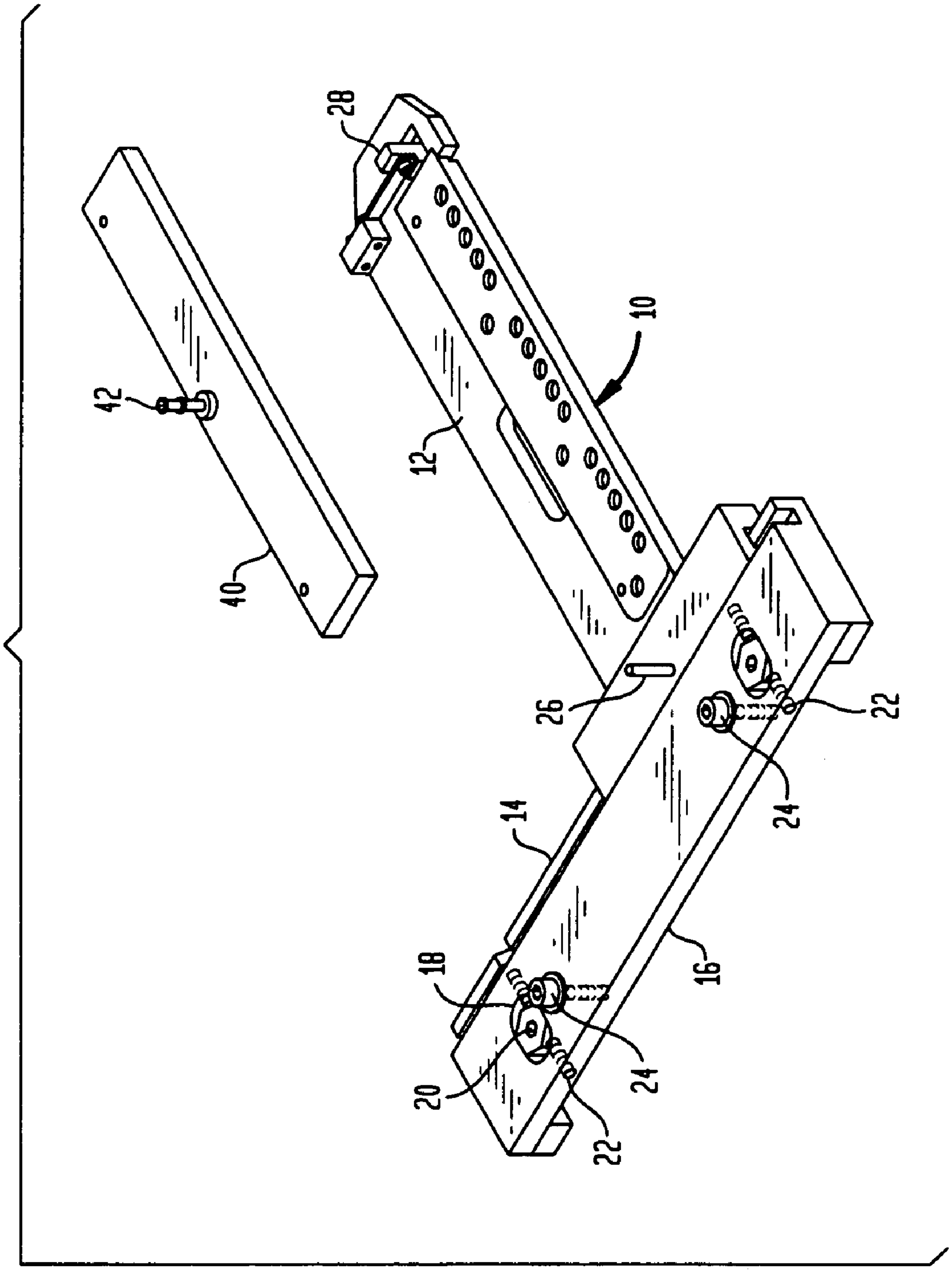
FIG. 3 is a diagrammatic perspective top view of this device and its associated cover.

The device shown in FIGS. 1 to 3 comprises a mask 10 in accordance with the invention, removably mounted on a support arm 12, substantially in the shape of a C, which is attached to and guided in translation on a rail 14 of a slide 16 for positioning and fixing on a plate (not shown) that carries the analytical support (for example agarose gel).

Slide 16 extends over one edge of this plate parallel to the direction of electrophoretic migration and comprises two transverse slots 18 in which are engaged hollow pins 20 carried by a further slide 21 that is integral with the edge of the plate, the hollows in pins 20 nesting into dogs emerging from the migration plate (not shown) and associated with screws 22 for adjusting the transverse position of slide 16 and thus of mask 10 with respect to the plate and analytical support. This slide also includes screws 24 that can lock the slide after adjustment.

Rail 14 extends parallel to the direction of electrophoretic migration and is engaged in a corresponding groove at one end of arm 16. This end carries a handle or rod 26 for translational displacement on rail 14 in one direction or the other.

In a variation, motorized means can be provided on slide 16 for automated displacement of arm 12, for example an electrical motor the drive shaft of which bears on a toothed wheel or pulley co-operating with a chain or belt respectively, connected to arm 12.

Mask 10 is fixed to arm 12 using any suitable means, for example an elastic snap fit as shown at 28, and is formed by a flat elongate substantially rectangular plate that extends transversely, i.e., perpendicular to the direction of electrophoretic migration.

This plate is held above the analytical support at a predetermined distance therefrom by projecting pins or blocks 30 formed on or fixed to the lower face of arm 12 and which are intended to rest on the edges of the plate described above.

The lower face of mask 10 comprises a series of oblique lanes (or ramps) 32, which are mutually parallel and arranged in two transverse rows that are mutually offset in a staggered pattern in the example shown. These lanes (or ramps) 32 extend parallel to the direction of electrophoretic migration and are all inclined in the same direction. Their lowest extremity comprises an orifice 34 for depositing the reagent on the analytical support. This orifice 34 is the lower orifice of a conduit or passage traversing the mask 10 over its whole thickness and opening into the upper face of the mask via an orifice 36 with a diameter that is much larger than that of the lower orifice 34.

Figure 4:
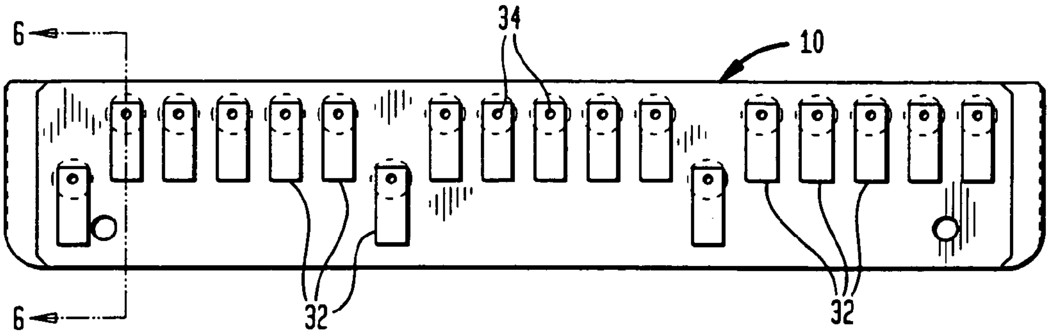
FIG. 4 is a view from below respectively of the mask of the invention.
Figure 5:
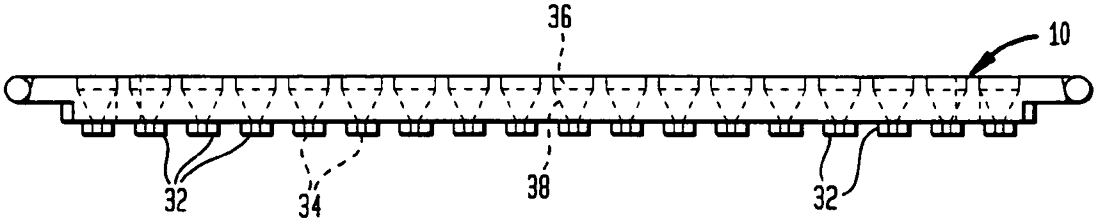
FIG. 5 is a view from the side of the mask of the invention.
Figure 6:
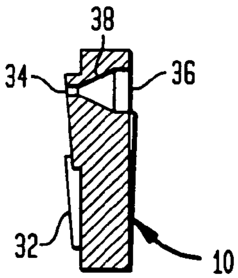
FIG. 6 is a cross-sectional view along line VI—VI of FIG. 4.

In one embodiment of the invention shown in FIGS. 4 to 6, these orifices 34 and 36 are the ends of small cylindrical conduits with a circular cross section connected to each other via a truncated conical conduit 38.

The mask holder 12 and snap fitted mask 10 are attached to guide rail 14, and so transverse adjustment using screw 22 can bring the ramps of the mask into vertical alignment with the sample migration lanes, which can be visualized by adding a suitable dye such as bromophenol blue to the deposited samples.

The mask can be manually swept over the top of the analytical support using handle 26 or using the motorized means described above.

As shown diagrammatically in FIG. 3, a cover 40 can be placed on the mask 10 and fixed thereon to close conduits 34, 36, 38 formed in mask 10 in a substantially sealed manner. A tube 42 on cover 40 opens above the upper orifices 36 of these conduits and allows injection of a small quantity of air between the mask and the cover, to exert a pressure on the reagents contained in the conduits of the mask and to cause them to fall into the conduits to bring them into contact with the analytical support.

The reagents can be deposited in the conduits of mask 10, these conduits can be closed in a substantially tight manner by cover 40, the mask 10/cover 40 assembly can be transported and placed above the analytical support before using the reagents.

Figure 7:
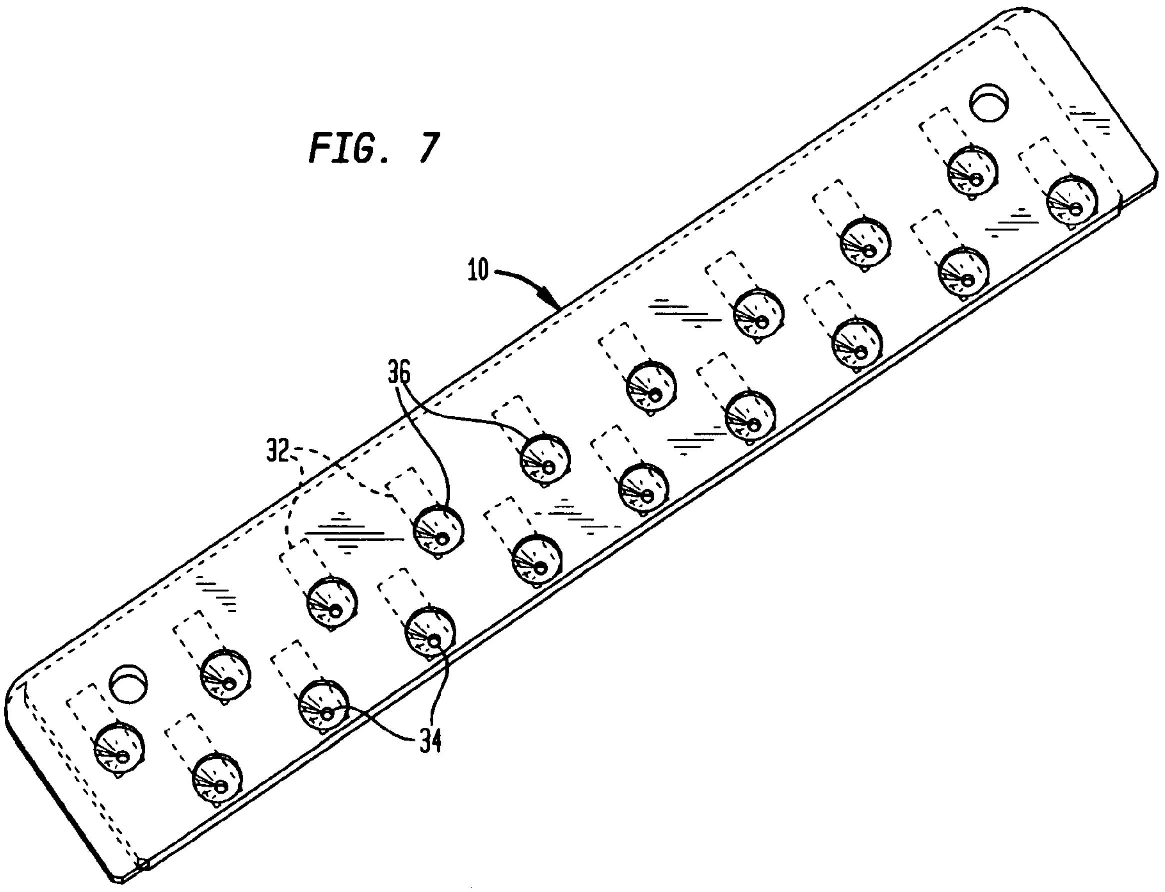
FIG. 7 is a diagrammatic perspective view of a variation of the invention.
Figure 8:
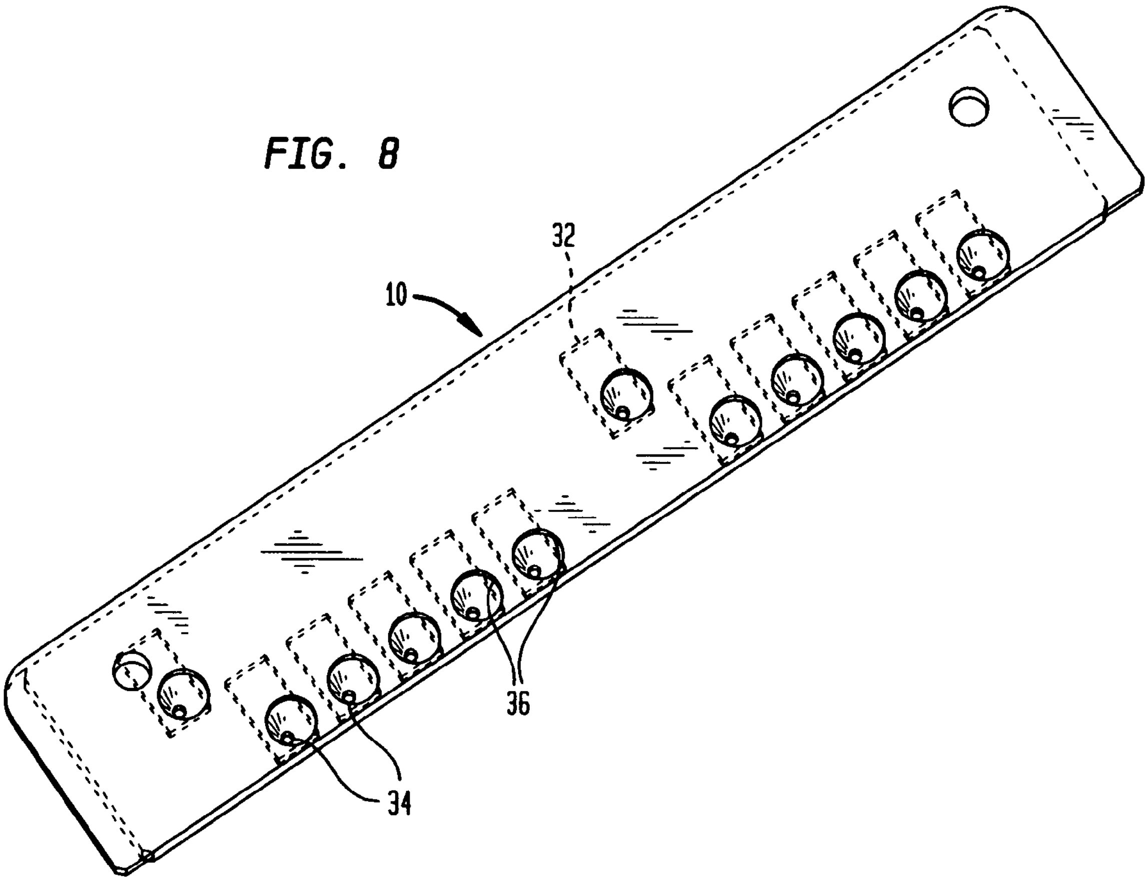
FIG. 8 is a diagrammatic perspective view of a variation of the invention.
Figure 9:
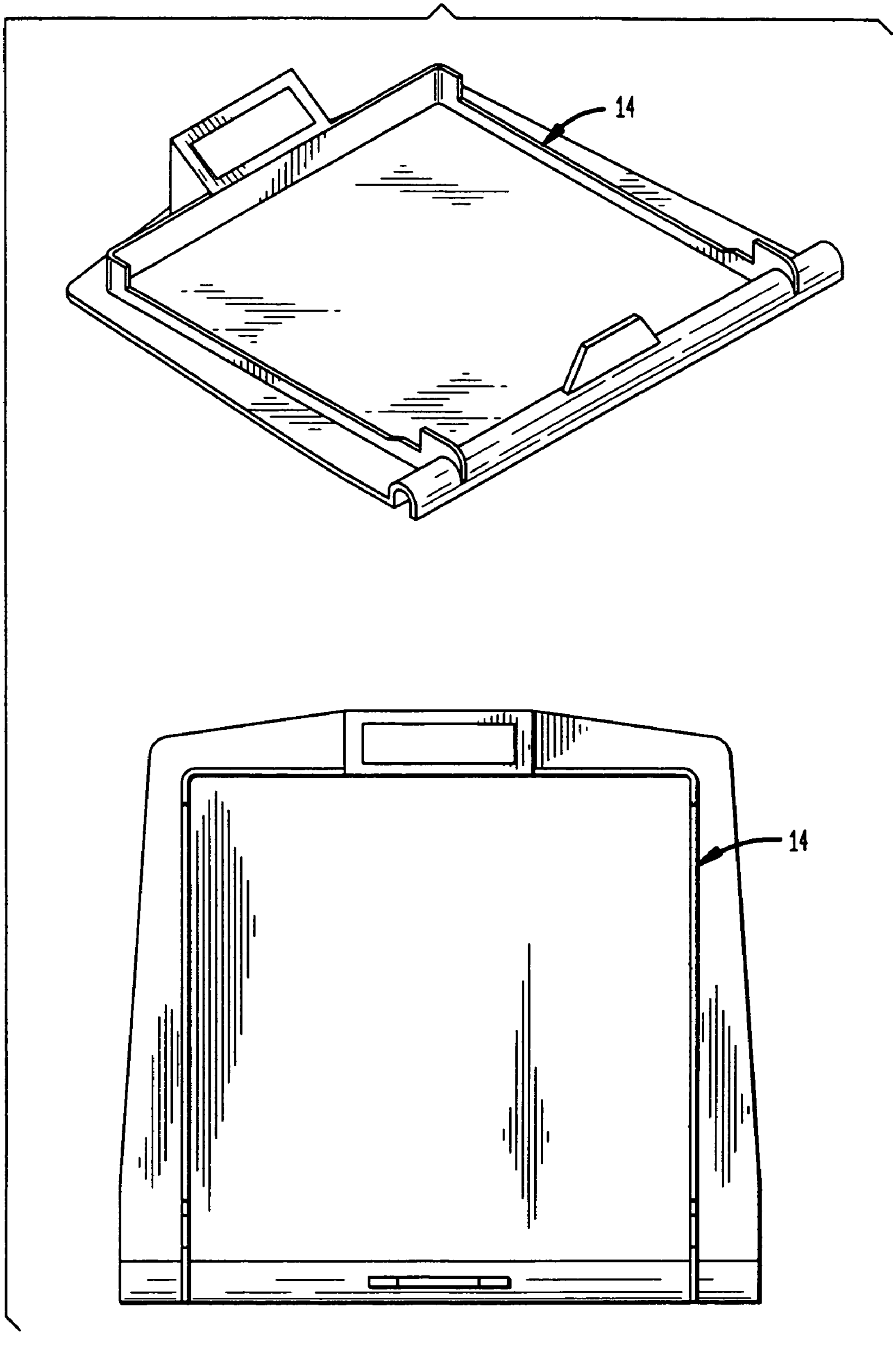
FIGS. 9 to 17 illustrate another embodiment of the invention where the lanes are formed in one row only.
Figure 10:
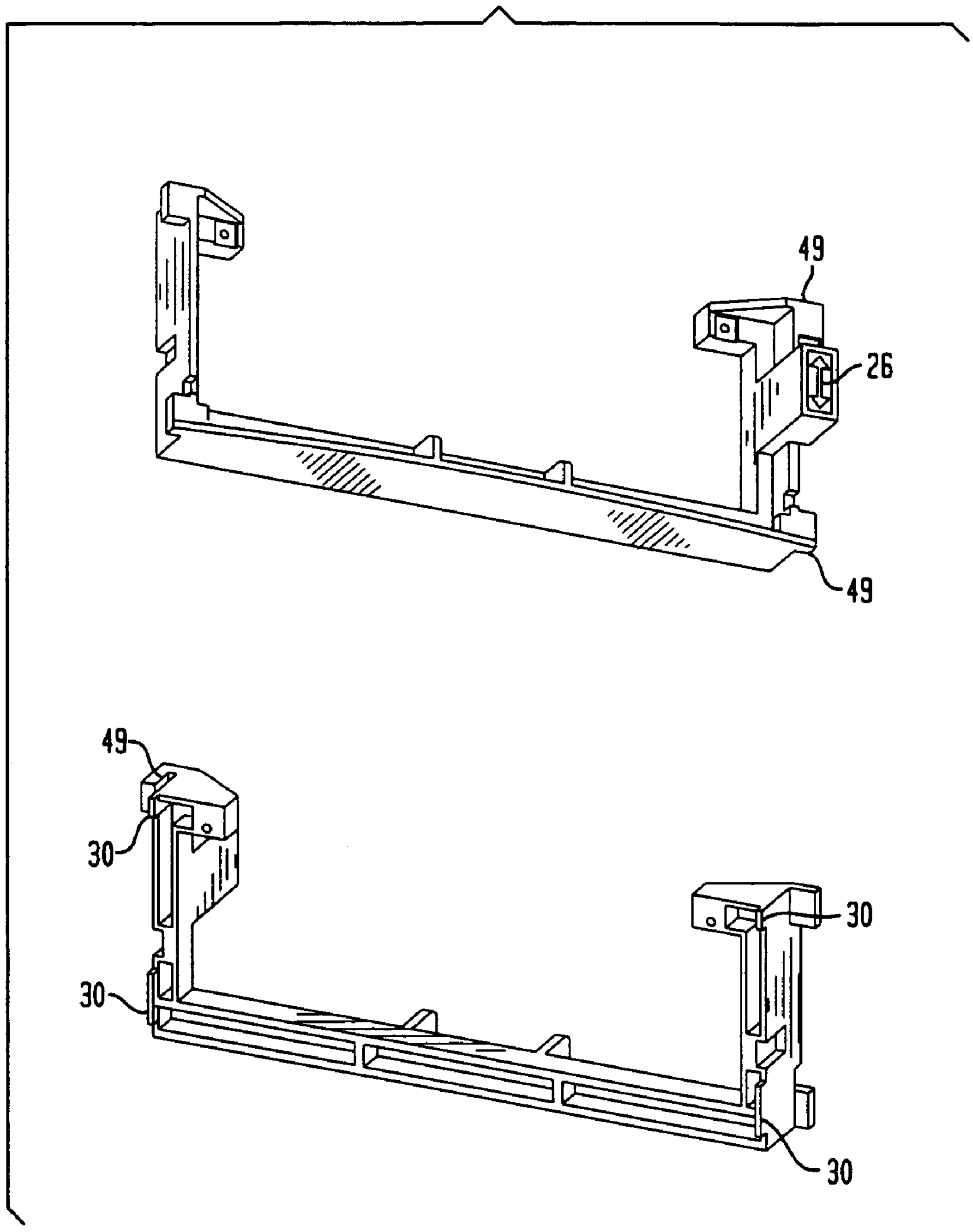
Figure 11:
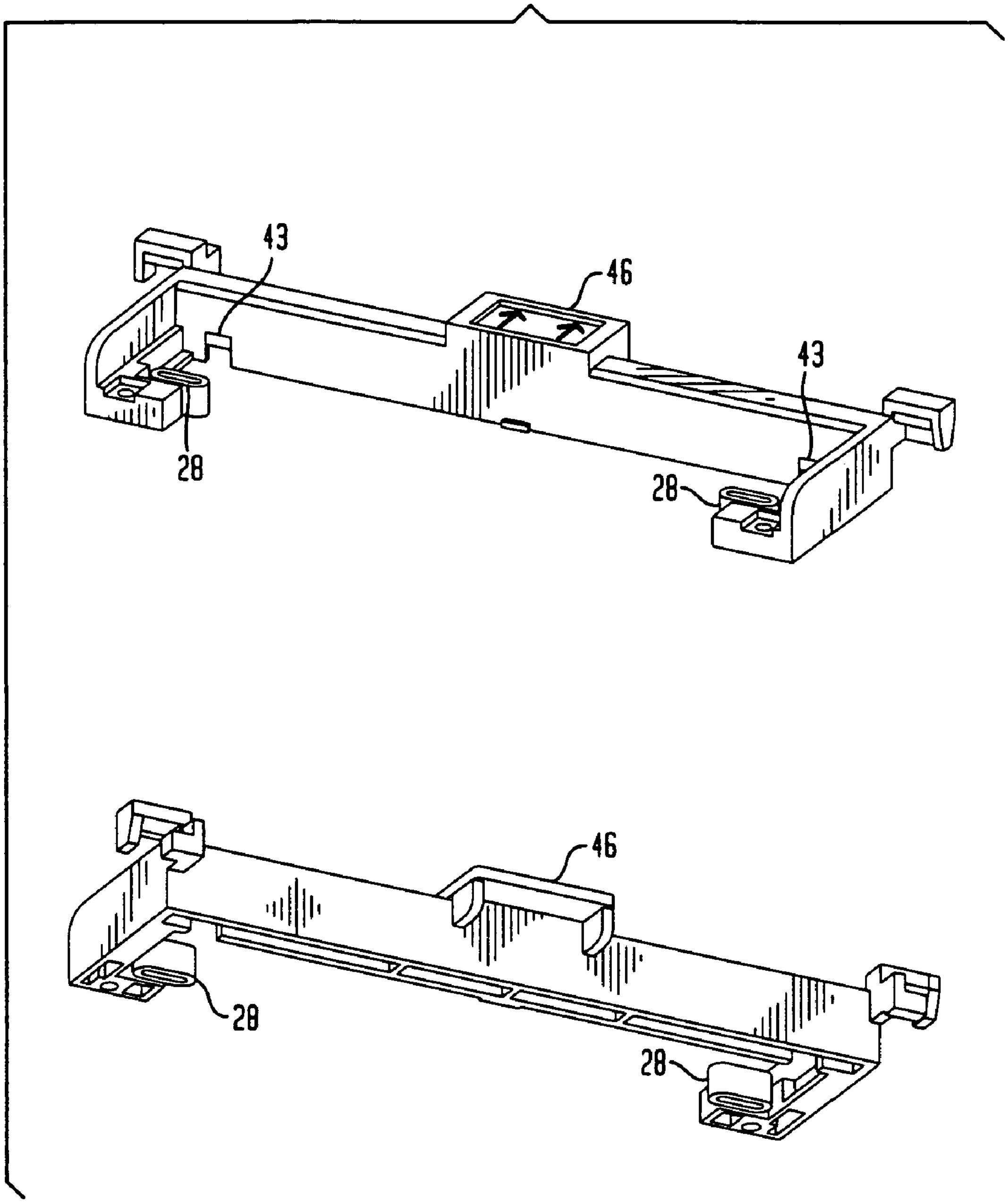
Figure 12:
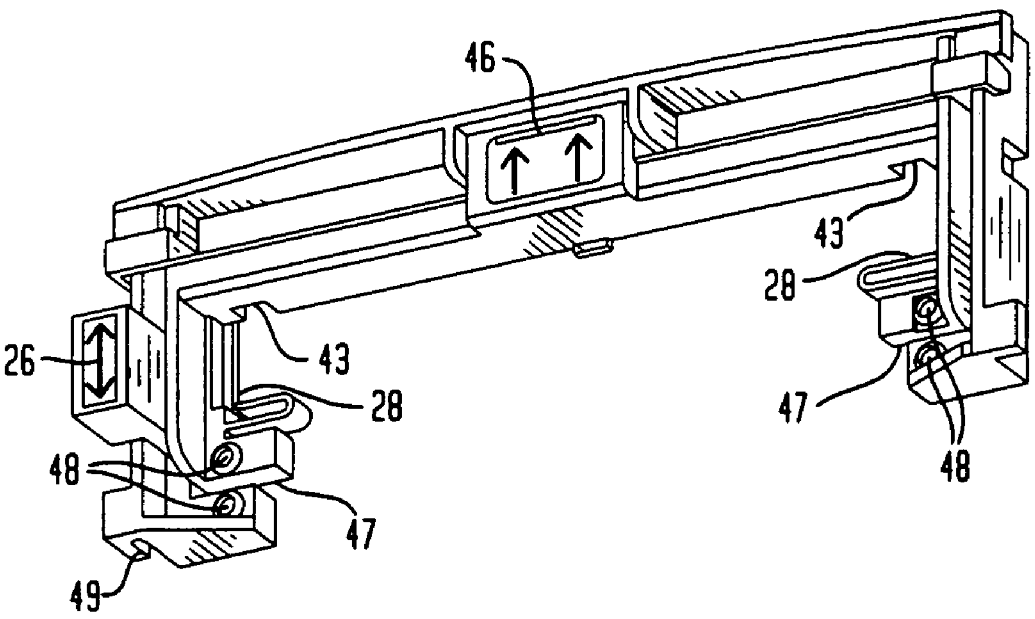

FIGS. 7 and 8 diagrammatically illustrate two variations of mask 10:

that of FIG. 7 comprises 18 traversing conduits arranged in two rows that are parallel and offset in a staggered pattern from one row to another;

that of FIG. 8 comprises two groups of six traversing conduits, the two groups being aligned over the length of the mask and each comprising five aligned conduits and one offset conduit.

EXAMPLES USING THE MASK OF THE INVENTION

Example 1

Simultaneous Immunofixation of 9 Samples Using a Mobile Mask with 18 Lanes (FIG. 4)

Manipulation was carried out using SEBIA's Hydrasys® electrophoresis instrument on a gel intended for immunofixation with dimensions of 0.7×83×101 mm.

To deposit samples on the electrophoresis support, we used applicators (French patent FR-A-2 671 290 and European patent EP-A-0 493 996) comprising 18×3 mm teeth spaced 2 mm apart. Each sample was deposited on 6 consecutive teeth, and thus each applicator could deposit 3 different samples on the electrophoresis gel, and 3 applicators were used to obtain the 9 samples for analysis. The deposits were made on the gel using the Hydrasys® instrument, in 3 parallel rows respectively located 18, 38 and 58 mm from the cathode edge of the gel. Electrophoretic migration was carried out at a controlled temperature of 20° C. at a constant power of 20 W and for a period so that 31 volt hours were accumulated.

Once migration was complete, the mobile mask of the invention with 18 lanes with the following geometrical characteristics was installed: lane width 2.5 mm, lane length 7 mm, inter-lane distance 2.5 mm, slope of lanes 5°. A row of 3 lanes (intended for the fixative) was offset by 5.5 mm with respect to the row of 15 lanes (intended for the antiserums).

The hollows in pins 20 of the guide rail were positioned on the two dogs carried on the migration plate of the Hydrasys® instrument.

The 18 lane mask was snap fitted into the mask holder 12, which itself had been attached to the guide rail. The mask and its mask holder were brought into abutment in the high position, i.e., on the anode side of the gel. A dye, bromophenol blue, incorporated into the samples deposited on the gel, allowed the position of the electrophoretic lanes on the analytical support to be visualized. Using transverse adjustment means 20, 22, the lanes or ramps of the mask were brought into vertical alignment with the migration lanes of the samples.

The mask was then loaded by introducing the different reagents required for immunofixation via the upper openings of the lanes (36), in an amount of 10 μl of reagent per lane and in the usual order: fixative, anti IgG, anti IgA, anti IgM, anti kappa and anti lambda. The fixative was introduced beneath the 3 offset anode side lanes.

Once introduced between the lanes and the gel, these 10 μl reagent loads were distributed beneath each lane over about 5–6 mm beyond the zones, anode side, that were to be revealed.

Once the mask had been loaded, it was displaced using the handle (26) by sliding along the guide rail. This sweep was carried out smoothly without jerking at an approximately constant speed from the high position (anode side) to the low position (cathode side) of the gel, over a path of 63 mm. This sweep was carried out in about 3 seconds.

Once the mask had arrived in abutment in the cathode position, a sweep was carried out in the reverse direction under the same conditions. These two sweeps were repeated once again. The entire amount of reagents initially introduced beneath the lanes had then been deposited on the gel above the electrophoretic migration zones. The mask could be withdrawn before the phase for incubating the reagents on the gel, carried out for 5 minutes at 20° C.

We then proceeded to the pumping, drying, washing, staining, destaining and drying steps using the usual immunofixation protocols.

Example 2

Simultaneous Immunofixation of 12 Samples Using a Mobile 18 Lane Mask (FIG. 4)

The procedure of the previous example was repeated, but 4 18 tooth applicators were loaded with 3 samples per applicator. Using the Hydrasys® instrument, deposits were made on the gel in 4 parallel rows respectively located 18, 33, 48 and 63 mm from the cathode edge of the gel. Migration was carried out for 28 volt hours at a constant power of 20 W, at 20° C. The method was then as described for the previous example.

Example 3

Simultaneous Immunofixation of 4 Samples Using a Mobile 12 Lane Mask (FIG. 8)

The samples were deposited on the gel using applicators with 15×4 mm wide teeth spaced apart by 2 mm, the applicators being loaded in an amount of 2 samples per applicator (sample no. 1, teeth 2 to 7; sample no. 2, teeth 9 to 14).

The Hydrasys® instrument was used to produce deposits on the gel in 2 parallel rows located respectively 23 and 53 mm from the cathode edge of the gel.

Migration at a controlled temperature of 20° C. at a constant power of 20 W was carried out until 42 volt hours had been accumulated.

Once migration was complete, the mobile mask of the invention with 12 lanes with the following geometrical characteristics was installed: lane width 3.5 mm, lane length 7 mm, inter-lane distance 2.5 mm, slope of lanes 5°. A row of 2 lanes (for loading the fixative) was offset by 5.5 mm with respect to the row of 10 lanes (for loading the antiserums).

The hollows in pins 20 of the guide rail were positioned on the two dogs carried by the migration plate of the Hydrasys® instrument. The 12 lane mask was snap fitted into the mask holder 12, which itself had been attached to the guide rail, and the assembly had been brought into abutment in the high position.

Using the transverse adjustment means, the lanes of the mask were brought (as described in Example 1) into alignment with the electrophoretic migration lanes of the samples.

The mask was loaded by introducing 14 μl of reagent per lane.

The reagents were distributed as described in the preceding examples by carrying out 4 sweeps with the mask.

The entire quantity of the reagents had then been deposited on the surface of the gel and the mask was then withdrawn.

We then proceeded to incubation and to the pumping, drying, washing, staining, destaining and drying steps using the usual immunofixation protocols.

Example 4

Carrying Out a 36 IF Penta Technique Using an 18 Lane Mobile Mask (FIG. 4)

The IF penta technique is routinely used to detect the presence of paraproteins in analyzed samples in the form of monoclonal or oligoclonal immunoglobulin bands.

This technique is carried out by side-by-side developing for each sample analyzed of the total protein profile and the profile of all immunoglobulins by carrying out immunofixation using a pentavalent antiserum, i.e., having anti IgG, anti IgA, anti IgM, anti kappa and anti lambda specificities.

Manipulation was carried out in this example using an agarose gel intended for immunofixation with dimensions 0.7×83×101 mm using a SEBIA Hydrasys® electrophoresis instrument. Combs with 18×3 mm teeth spaced 2 mm apart were used. Each sample for analysis was deposited twice side by side, i.e., 9 samples per applicator.

4 applicators were used for the 36 samples.

The deposits were made on the gel using the Hydrasys® instrument in 4 parallel rows respectively located 18, 33, 48 and 63 mm from the cathode edge of the gel. Migration was then carried out at a controlled temperature of 20° C. at a constant power of 20 W to an accumulation of 28 volt hours. The 18 lane mobile mask of the invention corresponding to FIG. 4 was then installed.

This mask was constituted by 2 rows of 9 lanes each, offset from each other by 5.5 mm. The 9 most anodic lanes were intended to receive the fixative and the 9 other lanes were intended to receive the pentavalent antiserum. Each lane was 2.5 mm wide, with a length of 7 mm, an inter-lane distance of 2.5 mm and a slope of 5°.

The mask was snap fitted in the mask holder and brought into abutment in the high anode side position.

The reagents were introduced in an amount of 10 μl/lane.

The procedure of Examples 1 to 3 was then followed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A mask for depositing and distributing reagents on an analytical support for biological samples, the mask comprising:

a body having a lower surface and an upper surface that are at least partially parallel and separated by a first distance constituting the thickness of the body;

at least one lane located on the lower surface of the body including a wedge-shaped projecting element, the projecting element having a first end and a second end, the first end disposed at a second distance from or coextensive with the lower surface of the body, and the second end disposed a third distance from the lower surface of the body, the third distance being greater than the second distance thereby forming a sloped surface between the first and second ends of the projecting element;

an opening associated with the at least one lane extending from the upper surface of the body to the sloped surface of the projecting element, the opening including an upper orifice on the upper surface of the body and a lower orifice on the sloped surface located in the proximity of the second end of the projecting element, wherein the lower orifice is located at the lowest point of the second end of the projecting element.

2. The mask according to claim 1 wherein the projecting element is of elongate shape.

3. The mask according to claim 1, wherein the mask is rigid or stiffened.

4. The mask according to claim 1, wherein the volume of the opening is such that it can constitute a reservoir for reagents loaded therein.

5. The mask according to claim 1, wherein the opening for the at least one lane is positioned perpendicular to the upper and lower surfaces of the body, the opening further including a first portion in the shape of a truncated cone having a first end with a first diameter and a second end with a second diameter, the first diameter being greater than the second diameter, the first end of the truncated cone forming the upper orifice.

6. The mask according to claim 5, wherein the opening further includes a second, cylindrical portion extending from the second end of the truncated cone.

7. The mask according to claim 1, comprising a plurality of the lanes disposed in parallel orientation along a length of the mask.

8. The mask according to claim 7, comprising:

a first series of the lanes in parallel orientation, each including one of the projecting elements, the projecting elements of the first series of lanes disposed in a first alignment at a first distance along the length of the mask;

a second series of the lanes arranged parallel to the lanes of the first series, the projecting elements of the second series of lanes disposed in a second alignment a second distance along the length of the mask and offset with respect to the first alignment.

9. The mask according to claim 1, in which the at least one lane has a length and the length of the sloped surface of the projecting element coincides with the length of the respective lane.

10. The mask according to claim 1, in which the mask has a plurality of lanes separated along a length of the mask from each other by a distance of 1.5 mm or more.

11. The mask according to claim 1, wherein the mask has a plurality of lanes, the lanes separated along a length of the mask by a distance sufficient such that reagents held between the mask and the analytical support by capillary action do not interact during distribution onto the analytical support.

12. The mask according to claim 1, in which the mask has a plurality of lanes, the lanes having a width of 2.5 mm.

13. The mask according to claim 1, in which the mask has a plurality of lanes, the lanes having a length in the range of 6 to 7 mm.

14. The mask according to claim 1, comprising a plurality of lanes, at least one lane is intended for a fixative and is offset with respect to a second, neighboring lane by a distance of 5 to 7 mm.

15. The mask according to claim 1, wherein the sloped surface is at an angle in the range of 1° to 10° to the lower surface of the body.

16. The mask according to claim 1, in which the at least one lane of the mask has:

a length of 3 to 15 mm;

a width of 1 to 10 mm; and an inclination of the sloped surface of 1° to 10° to the lower surface of the body of the mask.

17. A device for depositing and distributing one or more reagents on an analytical support for biological samples, comprising:

a mask according to claim 1; and positioning means for holding the mask in the proximity of the surface of the analytical support.

18. A device for depositing and distributing one or more reagents on an analytical support for biological samples, comprising:

a mask according to claim 1; and means for positioning and for guiding the mask thereby allowing the mask to be positioned so that the mask is held in the proximity of the surface of the analytical support and allowing the mask to be guided by sweeping the surface of the analytical support in a horizontal plane parallel to the lower surface of the support to allow deposition and distribution of the reagents over one or more predetermined zones of the analytical support coming into line with the lanes of the mask.

19. The mask according to claim 1, comprising a plurality of lanes and projecting elements having an opening therein, the mask further comprising at least one freeze dried reagent contained within the openings.

20. A method for depositing and distributing at least one reagent on an analytical support comprising biological samples, the method comprising:

positioning a mask according to claim 1 in the proximity of the analytical support;

loading at least one reagent into the mask to allow the reagent to be deposited on the analytical support and the reagent being held between the analytical support and the sloped surface of the projecting element by capillary action;

displacing the mask by sweeping the surface of the analytical support to distribute the at least one reagent on the analytical support in a delimited zone of the analytical support.

21. The method according to claim 20, wherein the at least one reagent is loaded in a quantity in the range of 4 to 15 μl in the opening of the mask, and wherein the mask is positioned a distance from the analytical support equal to or in the range of 0.1 to 0.5 mm from a point of the mask that is closest to the analytical support.

22. A method for depositing and distributing at least one reagent on an analytical support comprising biological samples, the method comprising:

loading the at least one reagent into a mask according to claim 1 to allow the reagent to be deposited on the analytical support and the reagent being held between the analytical support and the sloped surface of the projecting element by capillary action;

positioning the mask in the proximity of the analytical support to hold the at least one reagent on the analytical support between the analytical support and the sloped surface of the projecting element of the mask by capillary action;

displacing the mask by sweeping the surface of the analytical support to distribute the at least one reagent on the analytical support in a delimited zone of the analytical support.

23. The method according to claim 22, wherein the at least one reagent is loaded in a quantity equal to or in the range of 4 to 15 μl in the opening of the mask and wherein the mask is positioned a distance from the analytical support equal to or in the range of 0.1 to 0.5 mm from the point of the mask that is closest to the analytical support.

24. The method according to claim 22, in which the mask is loaded with the at least one reagent away from the surface of the analytical support.

25. The method according to claim 22, further including loading the mask with the at least one reagent prior to positioning the mask in the proximity of the analytical support, the at least one reagent being deposited on the analytical support by providing an impulse resulting from air pressure exerted on the mask, by a mechanical junction between the at least one reagent and the analytical support, by projecting the at least one reagent onto the analytical support, or by brief contact between the mask and the analytical support at the lowest point of the sloped surface of the lane.

26. The method according to claim 22, in which loading of the mask with the at least one reagent and/or displacement of the mask is automated.

27. The method according to claim 22, in which the analytical support is an electrophoresis support on which the constituents of at least one biological sample has been separated by electrophoretic migration.

28. The method according to claim 27, in which the at least one reagent is capable of immunofixation of the constituents of the biological samples separated by electrophoresis.

29. A method for detecting the constituents of at least one biological sample by immunofixation, comprising:

carrying out electrophoresis on an electrophoresis support of the at least one biological sample to separate out the constituents thereof;

depositing and distributing at least one reagent on an electrophoresis support using a method according to claim 20;

incubating the at least one biological sample separated by electrophoresis with the at least one reagent to allow their immunofixation.

30. A method for detecting the constituents of at least one biological sample by immunofixation, comprising:

carrying out electrophoresis on an electrophoresis support of the at least one biological sample to separate out the constituents thereof;

depositing and distributing at least reagent on the electrophoresis support using a method according to claim 22;

incubating the at least one biological sample separated by electrophoresis with the at least one reagent to allow their immunofixation.

31. A kit comprising:

at least one mask according to claim 1; and at least one analytical support.

32. The kit according to claim 31, further comprising:

at least one reagent for immunofixation of constituents of biological samples separated by electrophoresis;

a fixative for fixing constituents of a biological sample separated by electrophoresis.

* * * * *

UNITED STATES PATENT AND TRADEMARK OFFICE

CERTIFICATE OF CORRECTION

PATENT NO. : 7,048,893 B2
APPLICATION NO. : 10/359323
DATED : May 23, 2006
INVENTOR(S) : Franck Bellon It is certified that error appears in the above-identified patent and that said Letters Patent is hereby corrected as shown below:

On the Face of the Patent, in the last line of the Abstract, “incline with respect the” should read --incline with respect to the--.

Column 1, line10, after “abandoned” insert --,--.

Column 5, line 46, “enable to distribute” should read --enables distribution--.

Column 6, line 12, “are circular one.” should read --are circular.--

Column 12, line 66, “about 15 Ξl or 10 µl.” should read -- about 15 µl or 10 µl.--

Column 27, line 28, “freeze dried reagent” should read --freeze-dried reagent--.

Column 28, line 26, “biological sample has” should read --biological sample have--.

Column 28, line 50, “at least reagent” should read --at least one reagent--.

Signed and Sealed this

Thirty-first Day of October, 2006

JON W. DUDAS
*Director of the United States Patent and Trademark Office*